US007029851B2

United States Patent
Heckel et al.

(10) Patent No.: US 7,029,851 B2
(45) Date of Patent: Apr. 18, 2006

(54) **POLYNUCLEOTIDE ENCODING A GENE CONFERRING RESISTANCE TO *BACILLUS THURINGIENSIS* TOXINS**

(75) Inventors: David G. Heckel, Carlton (AU); Linda J. Gahan, Clemson, SC (US)

(73) Assignee: Clemson University, Clemson, SC (US)

( * ) Notice: Subject to any disclaimer, the term of this patent is extended or adjusted under 35 U.S.C. 154(b) by 528 days.

(21) Appl. No.: 10/098,916

(22) Filed: Mar. 15, 2002

(65) Prior Publication Data

US 2003/0096983 A1    May 22, 2003

Related U.S. Application Data

(60) Provisional application No. 60/276,180, filed on Mar. 15, 2001.

(51) Int. Cl.
*C12Q 1/68* (2006.01)
*C07H 21/02* (2006.01)
*C07H 21/04* (2006.01)

(52) U.S. Cl. .................. 435/6; 536/23.1; 536/24.3
(58) Field of Classification Search .............. 435/6; 530/350; 536/23.1, 24.3
See application file for complete search history.

(56) References Cited

U.S. PATENT DOCUMENTS

| | | | |
|---|---|---|---|
| 5,254,799 A | 10/1993 | De Greve et al. | |
| 5,349,124 A | 9/1994 | Fischhoff et al. | |
| 5,495,071 A | 2/1996 | Fischhoff et al. | |
| 5,608,142 A | 3/1997 | Barton et al. | |
| 5,693,491 A | 12/1997 | Bulla et al. | |
| 6,007,981 A | 12/1999 | Bulla | |
| 6,027,876 A | 2/2000 | Kreitman et al. | |
| 6,060,039 A | 5/2000 | Roe et al. | |
| 6,660,497 B1 | 12/2003 | Bulla, Jr. et al. | |
| 2003/0166891 A1 | 9/2003 | Flannagan et al. | |

FOREIGN PATENT DOCUMENTS

| | | |
|---|---|---|
| DE | 19819829 A1 | 11/1999 |
| WO | WO 98/59048 | 12/1998 |
| WO | WO 01/31011 A2 | 5/2001 |
| WO | WO 01/34807 A2 | 5/2001 |
| WO | WO 0136639 A2 | 5/2001 |
| WO | WO 0136639 A3 | 5/2001 |

OTHER PUBLICATIONS

Nagaraju, J, Identification of a gene associated with Bt resistance in the lepidopteran pest, *Heliothis virescens* and its implications in Bt transgenic-based pest control. Current Science. Oct. 10, 2001, vol. 81, No. 7, pp 746-747, United States.

International Search Report, PCT/US02/07872, pp 1-3, Sep. 12, 2002, United States.

International Search Report, PCT/US98/11868, pp. 1-3, Oct. 14, 1998; The Netherlands.

Gahan et al; "Identification of a Gene Associated with Bt Resistance in *Heliothis virescens*," American Association for the Advancement of Science, vol. 293, pp. 857-860, Aug. 3, 2001, United States.

Lander and Botstein, "Mapping Mendelian Factors Underlying Quantitative Traits Using RFLP Linkage Maps", Genetics 121:185-199, Jan., 1989, US.

Tabashnik et al, "Reversal of resistance to *Bacillus thuringienssis* in *Plutella xylostella*", Proc. Natl. Acad. Sci. USA, vol. 91, pp 4120-4124, May, 1994, US.

Gould et al, "Selection and Genetic Analysis of a *Heliothis virescens* (Lepidoptera: Noctuidae) Strain with High Levels of Resistance to *Bacillus thuringiensis* Toxins", J. of Economic Entomology, vol. 88, No. 6, pp 1545-1559, Dec., 1995, US.

Vadlamudi et al, "Cloning and Expression of a Receptor for an Insecticidal Toxin of *Bacillus thuringiensis*", J. of Biological Chemistry, vol. 270, No. 10, pp 5490-5494, Mar. 10, 1995, US.

Tabashnik, Commentary, "Seeking the root of insect resistance to transgenic plants", Proc. Natl. Acad. Sci. USA, vol. 94, pp 3488-3490, Apr., 1997, US.

Heckel, et al, "Identification of a Linkage Group with a Major Effect on Resistance to *Bacillus thuringiensis* Cry1Ac Endotoxin in the Tobacco Budworm (Lepidoptera: Noctuidae)", J. of Economic Entomology, vol. 90, No. 1, pp 75-86, 1997, US.

(Continued)

*Primary Examiner*—Ethan Whisenant
(74) *Attorney, Agent, or Firm*—Dority & Manning, P.A.

(57) ABSTRACT

Nucleic acid (DNA) probes are provided which will specifically identify a gene for resistance of Bt in insect populations. Sequences are identified associated with the onset of resistance to *Bacillus thuringiensis* toxins. The sequences are used as probes to monitor the presence of acquired insect resistance associated with transgenic crops.

7 Claims, 5 Drawing Sheets

OTHER PUBLICATIONS

Nagamatsu et al, "The cadherin-like protein is essential to specificity determination and cytotoxic action of the *Bacillus thuringiensis* insecticidal Cry1Aa toxin", Fed. of European Biochemical Societies, Letters 460 (1999) pp 385-390, Europe.

Abstract of Article—*Identification of Bombyx mori midgut receptor for Bacillus thuringiensis insecticidal CryIA(a) toxin,* Y. Nagamatsu, S. Toda, F. Yamaguchi, M. Ogo, M. Kogure, M. Nakamura, Y. Shibata, and T. Katsumoto, Biosci Biotechnol Biochem., vol. 62, No. 4, Apr. 1998, pp. 718-726, www.ncbi.nlm.nih.gov.

Article—*Identification of a Linkage Group with a Major Effect on Resistance to Bacillus thuringiensis Cry1Ac Endotoxin in the Tobacco Budworm (Lepidoptera: Noctuidae)*, David G. Heckel, Linda C. Gahan, Fred Gould, and Arne Anderson, Journal of Economic Entomology, vol. 90, No. 1, Feb. 1997, pp. 75-86.

SEQUENCE LISTING

<160> NUMBER OF SEQ ID NOS: 16

<210> SEQ ID NO 1
<211> LENGTH: 5355
<212> TYPE: DNA
<213> ORGANISM: Heliothis virescens
<220> FEATURE:
<221> NAME/KEY: CDS
<222> LOCATION: (10)..(5205)

<400> SEQUENCE: 1

```
aactatgag atg gca gtc gac gtg aga ata ctg acg gca gcg gta ttg att    51
         Met Ala Val Asp Val Arg Ile Leu Thr Ala Ala Val Leu Ile
           1               5                  10 ctc gct gct cat tta acg gtc gcg caa gat tgt tct tac atg gta gca      99
Leu Ala Ala His Leu Thr Val Ala Gln Asp Cys Ser Tyr Met Val Ala
 15              20                  25                  30 att cct aga cca gag cga cca gat ttt cct aat caa aat ttc gaa gga    147
Ile Pro Arg Pro Glu Arg Pro Asp Phe Pro Asn Gln Asn Phe Glu Gly
                 35                  40                  45 gta cca tgg agt cag aac ccc ctg tta cca gcg gag gat agg gaa gat    195
Val Pro Trp Ser Gln Asn Pro Leu Leu Pro Ala Glu Asp Arg Glu Asp
             50                  55                  60 gtg tgc atg aac gcg ttc gac ccg agt gcc ttg aac ccc gtc acc gtc    243
Val Cys Met Asn Ala Phe Asp Pro Ser Ala Leu Asn Pro Val Thr Val
         65                  70                  75 atc ttc atg gag gag gag atc gaa ggg gac gtg gcc att gcc agg ctt    291
Ile Phe Met Glu Glu Glu Ile Glu Gly Asp Val Ala Ile Ala Arg Leu
     80                  85                  90 aac tac cga ggt acc aat act ccg acc gtg gta act cca ttt aac ttt    339
Asn Tyr Arg Gly Thr Asn Thr Pro Thr Val Val Thr Pro Phe Asn Phe
 95                 100                 105                 110 ggt acc ttc cac ttg ttg ggg ccg gtc ata cgt agg atc ccc gag caa    387
Gly Thr Phe His Leu Leu Gly Pro Val Ile Arg Arg Ile Pro Glu Gln
                115                 120                 125 ggg ggg gac tgg cat ctt gtt att acg cag agg cag gac tat gag acc    435
Gly Gly Asp Trp His Leu Val Ile Thr Gln Arg Gln Asp Tyr Glu Thr
            130                 135                 140 ccg aac atg cag cag tat atc ttc aac gtg agg gta gaa gac gag ccc    483
Pro Asn Met Gln Gln Tyr Ile Phe Asn Val Arg Val Glu Asp Glu Pro
        145                 150                 155 cag gaa gcc act gtg atg ctc atc att gtc aac att gac gac aac gct    531
Gln Glu Ala Thr Val Met Leu Ile Ile Val Asn Ile Asp Asp Asn Ala
    160                 165                 170 cct atc ata cag atg ttc gag cct tgt gac att cct gaa cac ggc gaa    579
Pro Ile Ile Gln Met Phe Glu Pro Cys Asp Ile Pro Glu His Gly Glu
175                 180                 185                 190 acg ggc acc aca gaa tgc aag tac gtg gtg agc gat gct gac ggc gag    627
Thr Gly Thr Thr Glu Cys Lys Tyr Val Val Ser Asp Ala Asp Gly Glu
                195                 200                 205 atc agc aca cgt ttc atg acg ttc caa atc gag agc gat cga aac gat    675
Ile Ser Thr Arg Phe Met Thr Phe Gln Ile Glu Ser Asp Arg Asn Asp
            210                 215                 220 gaa gaa tat ttc gaa ctc gtc aga gag aat att cag gga cag tgg atg    723
Glu Glu Tyr Phe Glu Leu Val Arg Glu Asn Ile Gln Gly Gln Trp Met
        225                 230                 235 tac gtc cat atg agg ctt atc ctc aac aaa cct ctg gac tat gag gaa    771
Tyr Val His Met Arg Leu Ile Leu Asn Lys Pro Leu Asp Tyr Glu Glu
    240                 245                 250
```

```
                                                    -continued aac ccg ctg cat ttg ttt aga gtt aca gct ttg gat tcc cta cca aac      819
Asn Pro Leu His Leu Phe Arg Val Thr Ala Leu Asp Ser Leu Pro Asn
255                 260                 265                 270 gtt cac aca gta acg atg atg gtg caa gta gag aac ata gag agc aga      867
Val His Thr Val Thr Met Met Val Gln Val Glu Asn Ile Glu Ser Arg
                275                 280                 285 cca cca cgg tgg atg gag atc ttc gcc gtg cag cag ttc gat gag aag      915
Pro Pro Arg Trp Met Glu Ile Phe Ala Val Gln Gln Phe Asp Glu Lys
        290                 295                 300 aca gca caa gcc ttc agg gtt cga gcc atc gat gga gac acg gga atc      963
Thr Ala Gln Ala Phe Arg Val Arg Ala Ile Asp Gly Asp Thr Gly Ile
305                 310                 315 gat aaa cct att ttc tat agg atc gaa act gaa gaa agc gag aaa gat     1011
Asp Lys Pro Ile Phe Tyr Arg Ile Glu Thr Glu Glu Ser Glu Lys Asp
    320                 325                 330 ttg ttc agt gtt gaa aca ata gga gct ggt cgg gaa ggt gct tgg ttt     1059
Leu Phe Ser Val Glu Thr Ile Gly Ala Gly Arg Glu Gly Ala Trp Phe
335                 340                 345                 350 aaa gtc gct cca ata gac agg gac act cta gaa aag gaa gtt ttc cac     1107
Lys Val Ala Pro Ile Asp Arg Asp Thr Leu Glu Lys Glu Val Phe His
                355                 360                 365 gtg tct cta ata gcg tac aaa tat ggc gac aat gac gtg gaa gga agt     1155
Val Ser Leu Ile Ala Tyr Lys Tyr Gly Asp Asn Asp Val Glu Gly Ser
        370                 375                 380 ccg tca ttc gag tcg aag acc gat atc gtc att att gtg aac gac gtg     1203
Pro Ser Phe Glu Ser Lys Thr Asp Ile Val Ile Ile Val Asn Asp Val
385                 390                 395 aat gat cag gcg ccg gtg cca ttc cgt cct tca tac tac att gaa att     1251
Asn Asp Gln Ala Pro Val Pro Phe Arg Pro Ser Tyr Tyr Ile Glu Ile
    400                 405                 410 atg gag gaa gct gcg atg aca ttg aat tta gag gac ttt ggt ttc cac     1299
Met Glu Glu Ala Ala Met Thr Leu Asn Leu Glu Asp Phe Gly Phe His
415                 420                 425                 430 gat aga ggt ctt ggt ccg cac gca cag tac aca gtg cac ctg gag agc     1347
Asp Arg Gly Leu Gly Pro His Ala Gln Tyr Thr Val His Leu Glu Ser
                435                 440                 445 atc tcc ccg gcg gga gcg cac gag gcg ttc tac atc gcg ccg gag gtg     1395
Ile Ser Pro Ala Gly Ala His Glu Ala Phe Tyr Ile Ala Pro Glu Val
        450                 455                 460 ggc tac cag cga cag tcc ttc atc gtc ggc acg cag aac cat cac atg     1443
Gly Tyr Gln Arg Gln Ser Phe Ile Val Gly Thr Gln Asn His His Met
465                 470                 475 ctc gac ttt gaa gtg cca gag ttc caa aag ata caa ctt agg gcg gta     1491
Leu Asp Phe Glu Val Pro Glu Phe Gln Lys Ile Gln Leu Arg Ala Val
    480                 485                 490 gcc ata gac atg gac gat ccc agg tgg gtt ggt atc gcg att ata aac     1539
Ala Ile Asp Met Asp Asp Pro Arg Trp Val Gly Ile Ala Ile Ile Asn
495                 500                 505                 510 att aac ctg atc aac tgg aac gat gag ctg ccg atc ttc gag cac gac     1587
Ile Asn Leu Ile Asn Trp Asn Asp Glu Leu Pro Ile Phe Glu His Asp
                515                 520                 525 gtg cag act gtc acc ttc aag gag acg gag ggc gct ggc ttc cgg gtc     1635
Val Gln Thr Val Thr Phe Lys Glu Thr Glu Gly Ala Gly Phe Arg Val
        530                 535                 540 gcc act gtt ctg gca aag gac agg gat att gat gat aga gtc gaa cat     1683
Ala Thr Val Leu Ala Lys Asp Arg Asp Ile Asp Asp Arg Val Glu His
545                 550                 555 tct cta atg ggc aac gca gtg aac tac ctg agt atc gac aaa gac acc     1731
Ser Leu Met Gly Asn Ala Val Asn Tyr Leu Ser Ile Asp Lys Asp Thr
                565                 570
```

```
                                                              -continued ggc gac atc ctc gtg aca atc gac gat gca ttt aac tat cac aga cag    1779
Gly Asp Ile Leu Val Thr Ile Asp Asp Ala Phe Asn Tyr His Arg Gln
575                 580                 585                 590 aac gag ctc ttt gtg cag ata cga gct gat gac acg ttg gga gag ccg    1827
Asn Glu Leu Phe Val Gln Ile Arg Ala Asp Asp Thr Leu Gly Glu Pro
                595                 600                 605 tat aat acc aac acc gcc caa ctg gtg ata cag ctg caa gac atc aac    1875
Tyr Asn Thr Asn Thr Ala Gln Leu Val Ile Gln Leu Gln Asp Ile Asn
            610                 615                 620 aac aca cct cct acg ctc aga ctg cct cgc acg act ccg tca gtg gaa    1923
Asn Thr Pro Pro Thr Leu Arg Leu Pro Arg Thr Thr Pro Ser Val Glu
        625                 630                 635 gag aac gtg ccg gac ggg ttc gtg atc ccc acc gag ctg cac gcc acc    1971
Glu Asn Val Pro Asp Gly Phe Val Ile Pro Thr Glu Leu His Ala Thr
    640                 645                 650 gac ccc gac acc acc gcc gag ctg cgc ttc agc atc gac tgg gac act    2019
Asp Pro Asp Thr Thr Ala Glu Leu Arg Phe Ser Ile Asp Trp Asp Thr
655                 660                 665                 670 tcc tat gcc acc aag cag gga cga gat gct gat gct gag gag ttt gtt    2067
Ser Tyr Ala Thr Lys Gln Gly Arg Asp Ala Asp Ala Glu Glu Phe Val
                675                 680                 685 aat tgt ata gaa atc gag acg gta tac ccg aac ttg aac gac cga ggc    2115
Asn Cys Ile Glu Ile Glu Thr Val Tyr Pro Asn Leu Asn Asp Arg Gly
            690                 695                 700 acc gcc atc ggc cgc gtg gtg gtt cgc gag atc cgg gaa cac gtc acc    2163
Thr Ala Ile Gly Arg Val Val Val Arg Glu Ile Arg Glu His Val Thr
        705                 710                 715 atc gac tac gag atg ttc gag gtg ctg tac ctc acc gtc agg gtc acg    2211
Ile Asp Tyr Glu Met Phe Glu Val Leu Tyr Leu Thr Val Arg Val Thr
    720                 725                 730 gat ctc aac acg gtc att gga gac gac tat gat ata tca aca ttc acg    2259
Asp Leu Asn Thr Val Ile Gly Asp Asp Tyr Asp Ile Ser Thr Phe Thr
735                 740                 745                 750 atc att ata ata gac atg aac gac aac cct ccg ctg tgg gtg gaa ggc    2307
Ile Ile Ile Ile Asp Met Asn Asp Asn Pro Pro Leu Trp Val Glu Gly
                755                 760                 765 acg ctg acg cag gag ttc cgc gtg cga gag gtc gcc gcc tcg gga gtt    2355
Thr Leu Thr Gln Glu Phe Arg Val Arg Glu Val Ala Ala Ser Gly Val
            770                 775                 780 gtt ata gga tcc gta ctc gcc act gat atc gac gga cct ctt tat aat    2403
Val Ile Gly Ser Val Leu Ala Thr Asp Ile Asp Gly Pro Leu Tyr Asn
        785                 790                 795 caa gtg cgg tat acc atc act cct aga tta gat act cca gaa gac cta    2451
Gln Val Arg Tyr Thr Ile Thr Pro Arg Leu Asp Thr Pro Glu Asp Leu
    800                 805                 810 gtg gag atc gac ttc aat tcg ggt cag atc tca gtg aag aag cac cag    2499
Val Glu Ile Asp Phe Asn Ser Gly Gln Ile Ser Val Lys Lys His Gln
815                 820                 825                 830 gcc atc gac gcg gac gag ccg ccg cgc cag cac ctc tac tac acc gtg    2547
Ala Ile Asp Ala Asp Glu Pro Pro Arg Gln His Leu Tyr Tyr Thr Val
                835                 840                 845 gtc gcc agc gac aag tgc gac ctg ctc tct gtc gac gtg tgt ccg cct    2595
Val Ala Ser Asp Lys Cys Asp Leu Leu Ser Val Asp Val Cys Pro Pro
            850                 855                 860 gat cct aac tac ttc aac aca ccg gga gac ata acg atc cac ata aca    2643
Asp Pro Asn Tyr Phe Asn Thr Pro Gly Asp Ile Thr Ile His Ile Thr
        865                 870                 875 gac acg aac aac agg gtg cct cga gtg gaa gag gac aag ttc gag gaa    2691
Asp Thr Asn Asn Arg Val Pro Arg Val Glu Glu Asp Lys Phe Glu Glu
```

```
              880             885             890
att gtc tat atc tac gag ggc gcg gag gac gga gaa cac gtc gtg cag     2739
Ile Val Tyr Ile Tyr Glu Gly Ala Glu Asp Gly Glu His Val Val Gln
895             900             905             910 ctc ttc gcc agc gat ctg gat aga gat gaa atc tac cac aaa gtg agc     2787
Leu Phe Ala Ser Asp Leu Asp Arg Asp Glu Ile Tyr His Lys Val Ser
                915             920             925 tac cag atc aac tac gcg atc aac cct cgt ctc cgc gac ttc ttc gag     2835
Tyr Gln Ile Asn Tyr Ala Ile Asn Pro Arg Leu Arg Asp Phe Phe Glu
        930             935             940 gta gac ctg gag acc ggc ctg gtg tac gtc aac aac acg gcc ggg gag     2883
Val Asp Leu Glu Thr Gly Leu Val Tyr Val Asn Asn Thr Ala Gly Glu
    945             950             955 aag ctc gac cgg gac ggc gat gaa ccc acg cat cgg atc ttc ttc aac     2931
Lys Leu Asp Arg Asp Gly Asp Glu Pro Thr His Arg Ile Phe Phe Asn
960             965             970 gtt atc gat aac ttc tat ggg gaa gga gat ggc aac cgg aac cag gac     2979
Val Ile Asp Asn Phe Tyr Gly Glu Gly Asp Gly Asn Arg Asn Gln Asp
975             980             985             990 gag aca caa gtg tta gtg gtg ctg ttg gac atc aac gac aac tat ccg     3027
Glu Thr Gln Val Leu Val Val Leu Leu Asp Ile Asn Asp Asn Tyr Pro
                995             1000            1005 gag ctg cct gag ggt ctc tca tgg gat atc tct gag gga ttg cta cag     3075
Glu Leu Pro Glu Gly Leu Ser Trp Asp Ile Ser Glu Gly Leu Leu Gln
        1010            1015            1020 ggt gtc cgt gta acc cca gat atc ttc gcc ccg gac cgc gac gag ccc     3123
Gly Val Arg Val Thr Pro Asp Ile Phe Ala Pro Asp Arg Asp Glu Pro
    1025            1030            1035 ggc acc gac aac tcc cgc gtg gcg tac gac atc gtc agc ctc tcg ccc     3171
Gly Thr Asp Asn Ser Arg Val Ala Tyr Asp Ile Val Ser Leu Ser Pro
1040            1045            1050 acc gac agg gac atc aca ctt cct caa ctc ttc acc atg atc acc ata     3219
Thr Asp Arg Asp Ile Thr Leu Pro Gln Leu Phe Thr Met Ile Thr Ile
1055            1060            1065            1070 gag aag gac agg ggc atc gac cag act gga gag ctg gag acc gct atg     3267
Glu Lys Asp Arg Gly Ile Asp Gln Thr Gly Glu Leu Glu Thr Ala Met
                1075            1080            1085 gat tta aga ggc tat tgg ggc act tat gaa ata cat gta aag gca tac     3315
Asp Leu Arg Gly Tyr Trp Gly Thr Tyr Glu Ile His Val Lys Ala Tyr
        1090            1095            1100 gac cat gga gta cct caa agg att tcc tac gag aag tac ccg cta gtt     3363
Asp His Gly Val Pro Gln Arg Ile Ser Tyr Glu Lys Tyr Pro Leu Val
    1105            1110            1115 att aga cct tac aac ttc cac gac cct gtg ttc gtg ttc cct caa cct     3411
Ile Arg Pro Tyr Asn Phe His Asp Pro Val Phe Val Phe Pro Gln Pro
1120            1125            1130 gga atg act atc aga ctc gcg aag gag cga gca gta gtg aac gga gtg     3459
Gly Met Thr Ile Arg Leu Ala Lys Glu Arg Ala Val Val Asn Gly Val
1135            1140            1145            1150 ctg gcg aca gtg gac ggc gag ttc ctc gag cga ata gtc gcc acc gac     3507
Leu Ala Thr Val Asp Gly Glu Phe Leu Glu Arg Ile Val Ala Thr Asp
                1155            1160            1165 gag gat ggc tta cac gct gga gtt gtt acc ttc tct atc tcg gga gat     3555
Glu Asp Gly Leu His Ala Gly Val Val Thr Phe Ser Ile Ser Gly Asp
        1170            1175            1180 gat gag gcg ttg cag tac ttc gac gtg ttt aac gac gga gtg aac ttg     3603
Asp Glu Ala Leu Gln Tyr Phe Asp Val Phe Asn Asp Gly Val Asn Leu
    1185            1190            1195 ggt gcg ctg acc atc acg cag ctc ttc cct gaa gac ttc cga gag ttt     3651
```

```
                                                              -continued

Gly Ala Leu Thr Ile Thr Gln Leu Phe Pro Glu Asp Phe Arg Glu Phe
    1200                1205                1210 cag gtg acg att cgt gct acg gat ggt ggt acg gag cct ggt cca agg       3699
Gln Val Thr Ile Arg Ala Thr Asp Gly Gly Thr Glu Pro Gly Pro Arg
1215                1220                1225                1230 agt acc gac tgc acg atc acc gta gtg ttt gtg cct acg cag gga gag       3747
Ser Thr Asp Cys Thr Ile Thr Val Val Phe Val Pro Thr Gln Gly Glu
                1235                1240                1245 cct gtg ttc gaa act agc acc tac acg gtc gct ttt atc gag aaa gat       3795
Pro Val Phe Glu Thr Ser Thr Tyr Thr Val Ala Phe Ile Glu Lys Asp
            1250                1255                1260 gct ggt atg gaa gag cgg gcc acg ctg cct ctc gcc aag gac ccg cgt       3843
Ala Gly Met Glu Glu Arg Ala Thr Leu Pro Leu Ala Lys Asp Pro Arg
        1265                1270                1275 aac ata atg tgt gaa gat gat tgt cac gac acc tat tac agc att gtt       3891
Asn Ile Met Cys Glu Asp Asp Cys His Asp Thr Tyr Tyr Ser Ile Val
    1280                1285                1290 gga ggc aac tcg atg ggc cac ttt gcg gtg gac cct cag tcc aac gag       3939
Gly Gly Asn Ser Met Gly His Phe Ala Val Asp Pro Gln Ser Asn Glu
1295                1300                1305                1310 ctg ttc ctg ctg acg cca ctg gag cgc gcg gag cag gag acg cac acc       3987
Leu Phe Leu Leu Thr Pro Leu Glu Arg Ala Glu Gln Glu Thr His Thr
                1315                1320                1325 ctc atc atc ggc gcc agc gac tcg ccc agc cca gcc gcc gtg ctg cag       4035
Leu Ile Ile Gly Ala Ser Asp Ser Pro Ser Pro Ala Ala Val Leu Gln
            1330                1335                1340 gct tct acc ctc act gtt act gtc aat gtt cga gaa gca aac ccg cgg       4083
Ala Ser Thr Leu Thr Val Thr Val Asn Val Arg Glu Ala Asn Pro Arg
        1345                1350                1355 cca gtg ttc cag agc gct ctg tac aca gcc ggc atc tcc acc ctc gac       4131
Pro Val Phe Gln Ser Ala Leu Tyr Thr Ala Gly Ile Ser Thr Leu Asp
    1360                1365                1370 acc atc aac aga ggt ctg cta acg cta cac gcg act cat tca gaa ggc       4179
Thr Ile Asn Arg Gly Leu Leu Thr Leu His Ala Thr His Ser Glu Gly
1375                1380                1385                1390 ttg cct gtg acc tac acg ctg gta caa gac tcc atg gaa gct gac tcc       4227
Leu Pro Val Thr Tyr Thr Leu Val Gln Asp Ser Met Glu Ala Asp Ser
                1395                1400                1405 aca ctg caa gct gtg cag gag aca gcc ttc aac ttg aac cct cag act       4275
Thr Leu Gln Ala Val Gln Glu Thr Ala Phe Asn Leu Asn Pro Gln Thr
            1410                1415                1420 gga gtg ctg acc ctc aac ttc cag ccc aca gca tct atg cac ggc atg       4323
Gly Val Leu Thr Leu Asn Phe Gln Pro Thr Ala Ser Met His Gly Met
        1425                1430                1435 ttt gag ttc gat gtg atg gct act gat aca gtg gga gaa acc gcg cgc       4371
Phe Glu Phe Asp Val Met Ala Thr Asp Thr Val Gly Glu Thr Ala Arg
    1440                1445                1450 acc gaa gtg aag gtg tac ctg ata tcc gac cgc aac aga gtg ttc ttc       4419
Thr Glu Val Lys Val Tyr Leu Ile Ser Asp Arg Asn Arg Val Phe Phe
1455                1460                1465                1470 acg ttc atg aac acg ctt gaa gaa gtc gaa ccg aat gaa gat ttc ata       4467
Thr Phe Met Asn Thr Leu Glu Glu Val Glu Pro Asn Glu Asp Phe Ile
                1475                1480                1485 gcg gag aca ttt acc ctg ttc ttc ggc atg cgg tgc aac atc gac cag       4515
Ala Glu Thr Phe Thr Leu Phe Phe Gly Met Arg Cys Asn Ile Asp Gln
            1490                1495                1500 gcg ctg ccc gcc agc gac ccc gcc acc ggc gcc gcc agg gac gac cag       4563
Ala Leu Pro Ala Ser Asp Pro Ala Thr Gly Ala Ala Arg Asp Asp Gln
        1505                1510                1515
```

| | | |
|---|---|---|
| acc gaa gtc agg gca cac ttc ata cgc gac gac ctg cct gta cct gct<br>Thr Glu Val Arg Ala His Phe Ile Arg Asp Asp Leu Pro Val Pro Ala<br>    1520                     1525                  1530 | 4611 | |
| gag gag atc gaa caa tta cgc ggc aac ccg acc cta gtg gcg acc atc<br>Glu Glu Ile Glu Gln Leu Arg Gly Asn Pro Thr Leu Val Ala Thr Ile<br>1535                  1540                  1545                  1550 | 4659 | |
| cag aac gcc ctg cag gag gag aac ctg aac ctg gcc gac ctg ttc acg<br>Gln Asn Ala Leu Gln Glu Glu Asn Leu Asn Leu Ala Asp Leu Phe Thr<br>                 1555                  1560                  1565 | 4707 | |
| ggc gag act ccc atc ctg ggc ggc gag gcg cag gcg cgg gcg gtc tat<br>Gly Glu Thr Pro Ile Leu Gly Gly Glu Ala Gln Ala Arg Ala Val Tyr<br>1570                  1575                  1580 | 4755 | |
| gct ctc gcg gcg gtg gcg gct gcg ctc gcg ctg ctc tgc gtc gtg ctg<br>Ala Leu Ala Ala Val Ala Ala Ala Leu Ala Leu Leu Cys Val Val Leu<br>    1585                     1590                  1595 | 4803 | |
| ctt ata ctc ttc ttc atc agg act agg gcc ctc aac cgt cgc ctg gaa<br>Leu Ile Leu Phe Phe Ile Arg Thr Arg Ala Leu Asn Arg Arg Leu Glu<br>1600                  1605                  1610 | 4851 | |
| gcc cta tcc atg acc aag tac agt tcc caa gac tca gga ctc aac cgc<br>Ala Leu Ser Met Thr Lys Tyr Ser Ser Gln Asp Ser Gly Leu Asn Arg<br>1615                  1620                  1625                  1630 | 4899 | |
| gtg ggt ctg gcg gcg ccg ggc acc aac aag cac gcg gtg gag ggc tcc<br>Val Gly Leu Ala Ala Pro Gly Thr Asn Lys His Ala Val Glu Gly Ser<br>                 1635                  1640                  1645 | 4947 | |
| aac ccc atc tgg aac gaa act ctt aag gca ccg gac ttt gat gct ctt<br>Asn Pro Ile Trp Asn Glu Thr Leu Lys Ala Pro Asp Phe Asp Ala Leu<br>1650                  1655                  1660 | 4995 | |
| agc gag cag tcg tac gac tcg ggt ctg atc ggc atc gaa gac ttg ccg<br>Ser Glu Gln Ser Tyr Asp Ser Gly Leu Ile Gly Ile Glu Asp Leu Pro<br>    1665                     1670                  1675 | 5043 | |
| cag ttc agg aac gac tac ttc ccg cct gac gag gag agc tcc atg cgg<br>Gln Phe Arg Asn Asp Tyr Phe Pro Pro Asp Glu Glu Ser Ser Met Arg<br>1680                  1685                  1690 | 5091 | |
| gga gtc gtc aat gaa cac atg cct gga gct aat tca gta gca aac cat<br>Gly Val Val Asn Glu His Met Pro Gly Ala Asn Ser Val Ala Asn His<br>1695                  1700                  1705                  1710 | 5139 | |
| aac aat aac ttc ggg ttc aac gct acc ccc ttc agc cca gag ttc gcg<br>Asn Asn Asn Phe Gly Phe Asn Ala Thr Pro Phe Ser Pro Glu Phe Ala<br>                 1715                  1720                  1725 | 5187 | |
| aac tcg cag ctc agg aga taaaacatta tagtattttt tatataatat<br>Asn Ser Gln Leu Arg Arg<br>                1730 | 5235 | |
| tataagaag tgatataacg cactaaaatt tacctataag tatatattga agtgtaagat | 5295 | |
| actcgtatta tgtaagagca tctatttttt taccaccaga caataaaaac tttataaaag | 5355 | |

<210> SEQ ID NO 2
<211> LENGTH: 1732
<212> TYPE: PRT
<213> ORGANISM: Heliothis virescens

<400> SEQUENCE: 2

Met Ala Val Asp Val Arg Ile Leu Thr Ala Ala Val Leu Ile Leu Ala
  1               5                   10                 15

Ala His Leu Thr Val Ala Gln Asp Cys Ser Tyr Met Val Ala Ile Pro
               20                   25                 30

Arg Pro Glu Arg Pro Asp Phe Pro Asn Gln Asn Phe Glu Gly Val Pro
             35                   40                 45

Trp Ser Gln Asn Pro Leu Leu Pro Ala Glu Asp Arg Glu Asp Val Cys
 50                55                  60

-continued

```
Met Asn Ala Phe Asp Pro Ser Ala Leu Asn Pro Val Thr Val Ile Phe
 65                  70                  75                  80

Met Glu Glu Ile Glu Gly Asp Val Ala Ile Ala Arg Leu Asn Tyr
             85                  90                  95

Arg Gly Thr Asn Thr Pro Thr Val Val Thr Pro Phe Asn Phe Gly Thr
                100                 105                 110

Phe His Leu Leu Gly Pro Val Ile Arg Arg Ile Pro Glu Gln Gly Gly
            115                 120                 125

Asp Trp His Leu Val Ile Thr Gln Arg Gln Asp Tyr Glu Thr Pro Asn
    130                 135                 140

Met Gln Gln Tyr Ile Phe Asn Val Arg Val Glu Asp Glu Pro Gln Glu
145                 150                 155                 160

Ala Thr Val Met Leu Ile Ile Val Asn Ile Asp Asp Asn Ala Pro Ile
                165                 170                 175

Ile Gln Met Phe Glu Pro Cys Asp Ile Pro Glu His Gly Glu Thr Gly
            180                 185                 190

Thr Thr Glu Cys Lys Tyr Val Val Ser Asp Ala Asp Gly Glu Ile Ser
        195                 200                 205

Thr Arg Phe Met Thr Phe Gln Ile Glu Ser Asp Arg Asn Asp Glu Glu
    210                 215                 220

Tyr Phe Glu Leu Val Arg Glu Asn Ile Gln Gly Gln Trp Met Tyr Val
225                 230                 235                 240

His Met Arg Leu Ile Leu Asn Lys Pro Leu Asp Tyr Glu Glu Asn Pro
                245                 250                 255

Leu His Leu Phe Arg Val Thr Ala Leu Asp Ser Leu Pro Asn Val His
            260                 265                 270

Thr Val Thr Met Met Val Gln Val Glu Asn Ile Glu Ser Arg Pro Pro
        275                 280                 285

Arg Trp Met Glu Ile Phe Ala Val Gln Gln Phe Asp Glu Lys Thr Ala
    290                 295                 300

Gln Ala Phe Arg Val Arg Ala Ile Asp Gly Asp Thr Gly Ile Asp Lys
305                 310                 315                 320

Pro Ile Phe Tyr Arg Ile Glu Thr Glu Glu Ser Glu Lys Asp Leu Phe
                325                 330                 335

Ser Val Glu Thr Ile Gly Ala Gly Arg Glu Gly Ala Trp Phe Lys Val
            340                 345                 350

Ala Pro Ile Asp Arg Asp Thr Leu Glu Lys Glu Val Phe His Val Ser
        355                 360                 365

Leu Ile Ala Tyr Lys Tyr Gly Asp Asn Asp Val Glu Gly Ser Pro Ser
    370                 375                 380

Phe Glu Ser Lys Thr Asp Ile Val Ile Val Asn Asp Val Asn Asp
385                 390                 395                 400

Gln Ala Pro Val Pro Phe Arg Pro Ser Tyr Tyr Ile Glu Ile Met Glu
                405                 410                 415

Glu Ala Ala Met Thr Leu Asn Leu Glu Asp Phe Gly Phe His Asp Arg
            420                 425                 430

Gly Leu Gly Pro His Ala Gln Tyr Thr Val His Leu Glu Ser Ile Ser
        435                 440                 445

Pro Ala Gly Ala His Glu Ala Phe Tyr Ile Ala Pro Glu Val Gly Tyr
    450                 455                 460

Gln Arg Gln Ser Phe Ile Val Gly Thr Gln Asn His His Met Leu Asp
465                 470                 475                 480
```

-continued

```
Phe Glu Val Pro Glu Phe Gln Lys Ile Gln Leu Arg Ala Val Ala Ile
                485                 490                 495

Asp Met Asp Asp Pro Arg Trp Val Gly Ile Ala Ile Ile Asn Ile Asn
            500                 505                 510

Leu Ile Asn Trp Asn Asp Glu Leu Pro Ile Phe Glu His Asp Val Gln
        515                 520                 525

Thr Val Thr Phe Lys Glu Thr Glu Gly Ala Gly Phe Arg Val Ala Thr
    530                 535                 540

Val Leu Ala Lys Asp Arg Asp Ile Asp Asp Arg Val Glu His Ser Leu
545                 550                 555                 560

Met Gly Asn Ala Val Asn Tyr Leu Ser Ile Asp Lys Asp Thr Gly Asp
                565                 570                 575

Ile Leu Val Thr Ile Asp Asp Ala Phe Asn Tyr His Arg Gln Asn Glu
            580                 585                 590

Leu Phe Val Gln Ile Arg Ala Asp Asp Thr Leu Gly Glu Pro Tyr Asn
        595                 600                 605

Thr Asn Thr Ala Gln Leu Val Ile Gln Leu Gln Asp Ile Asn Asn Thr
    610                 615                 620

Pro Pro Thr Leu Arg Leu Pro Arg Thr Thr Pro Ser Val Glu Glu Asn
625                 630                 635                 640

Val Pro Asp Gly Phe Val Ile Pro Thr Glu Leu His Ala Thr Asp Pro
                645                 650                 655

Asp Thr Thr Ala Glu Leu Arg Phe Ser Ile Asp Trp Asp Thr Ser Tyr
            660                 665                 670

Ala Thr Lys Gln Gly Arg Asp Ala Asp Ala Glu Glu Phe Val Asn Cys
        675                 680                 685

Ile Glu Ile Glu Thr Val Tyr Pro Asn Leu Asn Asp Arg Gly Thr Ala
    690                 695                 700

Ile Gly Arg Val Val Val Arg Glu Ile Arg Glu His Val Thr Ile Asp
705                 710                 715                 720

Tyr Glu Met Phe Glu Val Leu Tyr Leu Thr Val Arg Val Thr Asp Leu
                725                 730                 735

Asn Thr Val Ile Gly Asp Asp Tyr Asp Ile Ser Thr Phe Thr Ile Ile
            740                 745                 750

Ile Ile Asp Met Asn Asp Asn Pro Pro Leu Trp Val Glu Gly Thr Leu
        755                 760                 765

Thr Gln Glu Phe Arg Val Arg Glu Val Ala Ala Ser Gly Val Val Ile
    770                 775                 780

Gly Ser Val Leu Ala Thr Asp Ile Asp Gly Pro Leu Tyr Asn Gln Val
785                 790                 795                 800

Arg Tyr Thr Ile Thr Pro Arg Leu Asp Thr Pro Glu Asp Leu Val Glu
                805                 810                 815

Ile Asp Phe Asn Ser Gly Gln Ile Ser Val Lys Lys His Gln Ala Ile
            820                 825                 830

Asp Ala Asp Glu Pro Pro Arg Gln His Leu Tyr Tyr Thr Val Val Ala
        835                 840                 845

Ser Asp Lys Cys Asp Leu Leu Ser Val Asp Val Cys Pro Pro Asp Pro
    850                 855                 860

Asn Tyr Phe Asn Thr Pro Gly Asp Ile Thr Ile His Ile Thr Asp Thr
865                 870                 875                 880

Asn Asn Arg Val Pro Arg Val Glu Glu Asp Lys Phe Glu Glu Ile Val
                885                 890                 895

Tyr Ile Tyr Glu Gly Ala Glu Asp Gly Glu His Val Val Gln Leu Phe
```

-continued

```
                 900                 905                 910
Ala Ser Asp Leu Asp Arg Asp Glu Ile Tyr His Lys Val Ser Tyr Gln
            915                 920                 925
Ile Asn Tyr Ala Ile Asn Pro Arg Leu Arg Asp Phe Phe Glu Val Asp
            930                 935                 940
Leu Glu Thr Gly Leu Val Tyr Val Asn Asn Thr Ala Gly Glu Lys Leu
945                 950                 955                 960
Asp Arg Asp Gly Asp Glu Pro Thr His Arg Ile Phe Phe Asn Val Ile
                965                 970                 975
Asp Asn Phe Tyr Gly Glu Gly Asp Gly Asn Arg Asn Gln Asp Glu Thr
            980                 985                 990
Gln Val Leu Val Val Leu Leu Asp Ile Asn Asp Asn Tyr Pro Glu Leu
            995                 1000                1005
Pro Glu Gly Leu Ser Trp Asp Ile Ser Glu Gly Leu Leu Gln Gly Val
        1010                1015                1020
Arg Val Thr Pro Asp Ile Phe Ala Pro Asp Arg Asp Glu Pro Gly Thr
1025                1030                1035                1040
Asp Asn Ser Arg Val Ala Tyr Asp Ile Val Ser Leu Ser Pro Thr Asp
                1045                1050                1055
Arg Asp Ile Thr Leu Pro Gln Leu Phe Thr Met Ile Thr Ile Glu Lys
            1060                1065                1070
Asp Arg Gly Ile Asp Gln Thr Gly Glu Leu Glu Thr Ala Met Asp Leu
        1075                1080                1085
Arg Gly Tyr Trp Gly Thr Tyr Glu Ile His Val Lys Ala Tyr Asp His
        1090                1095                1100
Gly Val Pro Gln Arg Ile Ser Tyr Glu Lys Tyr Pro Leu Val Ile Arg
1105                1110                1115                1120
Pro Tyr Asn Phe His Asp Pro Val Phe Val Phe Pro Gln Pro Gly Met
                1125                1130                1135
Thr Ile Arg Leu Ala Lys Glu Arg Ala Val Val Asn Gly Val Leu Ala
            1140                1145                1150
Thr Val Asp Gly Glu Phe Leu Glu Arg Ile Val Ala Thr Asp Glu Asp
        1155                1160                1165
Gly Leu His Ala Gly Val Val Thr Phe Ser Ile Ser Gly Asp Asp Glu
        1170                1175                1180
Ala Leu Gln Tyr Phe Asp Val Phe Asn Asp Gly Val Asn Leu Gly Ala
1185                1190                1195                1200
Leu Thr Ile Thr Gln Leu Phe Pro Glu Asp Phe Arg Glu Phe Gln Val
            1205                1210                1215
Thr Ile Arg Ala Thr Asp Gly Gly Thr Glu Pro Gly Pro Arg Ser Thr
            1220                1225                1230
Asp Cys Thr Ile Thr Val Val Phe Val Pro Thr Gln Gly Glu Pro Val
        1235                1240                1245
Phe Glu Thr Ser Thr Tyr Thr Val Ala Phe Ile Glu Lys Asp Ala Gly
        1250                1255                1260
Met Glu Glu Arg Ala Thr Leu Pro Leu Ala Lys Asp Pro Arg Asn Ile
1265                1270                1275                1280
Met Cys Glu Asp Asp Cys His Asp Thr Tyr Tyr Ser Ile Val Gly Gly
                1285                1290                1295
Asn Ser Met Gly His Phe Ala Val Asp Pro Gln Ser Asn Glu Leu Phe
            1300                1305                1310
Leu Leu Thr Pro Leu Glu Arg Ala Glu Gln Glu Thr His Thr Leu Ile
            1315                1320                1325
```

```
Ile Gly Ala Ser Asp Ser Pro Ser Pro Ala Ala Val Leu Gln Ala Ser
    1330                1335                1340

Thr Leu Thr Val Thr Val Asn Val Arg Glu Ala Asn Pro Arg Pro Val
1345                1350                1355                1360

Phe Gln Ser Ala Leu Tyr Thr Ala Gly Ile Ser Thr Leu Asp Thr Ile
                1365                1370                1375

Asn Arg Gly Leu Leu Thr Leu His Ala Thr His Ser Glu Gly Leu Pro
            1380                1385                1390

Val Thr Tyr Thr Leu Val Gln Asp Ser Met Glu Ala Asp Ser Thr Leu
        1395                1400                1405

Gln Ala Val Gln Glu Thr Ala Phe Asn Leu Asn Pro Gln Thr Gly Val
    1410                1415                1420

Leu Thr Leu Asn Phe Gln Pro Thr Ala Ser Met His Gly Met Phe Glu
1425                1430                1435                1440

Phe Asp Val Met Ala Thr Asp Thr Val Gly Glu Thr Ala Arg Thr Glu
                1445                1450                1455

Val Lys Val Tyr Leu Ile Ser Asp Arg Asn Arg Val Phe Phe Thr Phe
            1460                1465                1470

Met Asn Thr Leu Glu Glu Val Glu Pro Asn Glu Asp Phe Ile Ala Glu
        1475                1480                1485

Thr Phe Thr Leu Phe Phe Gly Met Arg Cys Asn Ile Asp Gln Ala Leu
    1490                1495                1500

Pro Ala Ser Asp Pro Ala Thr Gly Ala Ala Arg Asp Asp Gln Thr Glu
1505                1510                1515                1520

Val Arg Ala His Phe Ile Arg Asp Asp Leu Pro Val Pro Ala Glu Glu
                1525                1530                1535

Ile Glu Gln Leu Arg Gly Asn Pro Thr Leu Val Ala Thr Ile Gln Asn
            1540                1545                1550

Ala Leu Gln Glu Glu Asn Leu Asn Leu Ala Asp Leu Phe Thr Gly Glu
        1555                1560                1565

Thr Pro Ile Leu Gly Gly Glu Ala Gln Ala Arg Ala Val Tyr Ala Leu
    1570                1575                1580

Ala Ala Val Ala Ala Ala Leu Ala Leu Leu Cys Val Val Leu Leu Ile
1585                1590                1595                1600

Leu Phe Phe Ile Arg Thr Arg Ala Leu Asn Arg Arg Leu Glu Ala Leu
                1605                1610                1615

Ser Met Thr Lys Tyr Ser Ser Gln Asp Ser Gly Leu Asn Arg Val Gly
            1620                1625                1630

Leu Ala Ala Pro Gly Thr Asn Lys His Ala Val Glu Gly Ser Asn Pro
        1635                1640                1645

Ile Trp Asn Glu Thr Leu Lys Ala Pro Asp Phe Asp Ala Leu Ser Glu
    1650                1655                1660

Gln Ser Tyr Asp Ser Gly Leu Ile Gly Ile Glu Asp Leu Pro Gln Phe
1665                1670                1675                1680

Arg Asn Asp Tyr Phe Pro Pro Asp Glu Glu Ser Ser Met Arg Gly Val
                1685                1690                1695

Val Asn Glu His Met Pro Gly Ala Asn Ser Val Ala Asn His Asn Asn
            1700                1705                1710

Asn Phe Gly Phe Asn Ala Thr Pro Phe Ser Pro Glu Phe Ala Asn Ser
        1715                1720                1725

Gln Leu Arg Arg
    1730
```

-continued

<210> SEQ ID NO 3
<211> LENGTH: 7799
<212> TYPE: DNA
<213> ORGANISM: Heliothis virescens

<400> SEQUENCE: 3
gatcgactag tgaattgttg tttcaaaaaa gcaagaaatt acgtagttct aaaaataaaa 60
gtgtttttgt gtaaagtgta gtgctaaaga acttggcatt gtttgaagag gattaaaagg 120
agtccaaatt gatcacacgc aggtggatct accaggctag agacacgaga tacgacagag 180
tgagaactat gagatggcag tcgacgtgag aatactgacg gcagcggtat tgattctcgc 240
tgctaattta actttcgcgc aagattgttc ctatatggta gcaattccca gaccagagcg 300
accagacttt cctaatcaaa atttcgaagg agtaccatgg agtcagaacc ctctattacc 360
agcggaggat agggaagatg tgtgcatgaa cgcgtttgat ccaagtgcct tgaaccccgt 420
caccgtcatc ttcatggagg aggagatcga aggggacgtg gccattgcca ggcttaacta 480
ccgaggtacc aatactccga ccgtggtaac tccatttaac tttggtacct tccacttgtt 540
ggggccggtc atacgtagga tccccgagca agggggggac tggcatcttg ttattacgca 600
gaggcaggac tatgagaccc cgaacatgca gcagtatatc ttcaacgtga gggtagaaga 660
tgagccccag gaagccactg tgatgctcat cattgtcaac atcgacgaca acgctcctat 720
gatacagatg ttcgagcctt gtgacattcc tgaacacggc gaaacgggca ccacagaatg 780
caagtccgtg gtgagcgatg ctgacggcga gatcagcaca cgtttcatga cgttcgaaat 840
cgagagcgat cgaaacgacg aagaatattt cgaacttgtc agagagaata ttcagggaca 900
gtggatgtac gtccatatga ggctcatcct caacaaacct ctggactatg aggaaaaccc 960
gctgcatttg tttagagtta cagctttgga ttccctaccg aacgttcata cagtgactat 1020
gatggtgcaa gtcgagaaca tagagagcag accgccgcgg tggatggaga tcttcgccgt 1080
gcagcagttc gatgagaaga cagcacaatc cttcagggtt cgagccatcg atggagacac 1140
gggaatcgat aaacctattt tctataggat cgaaactgaa gaaagcgaga aagatctgtt 1200
cagtgttgaa acaatagggg ctggtcggga aggtgcttgg tttaaagtcg ctccaataga 1260
cagagacacc cttgaaaagg aagttttcca cgtgtctcta attgcgtaca aatatggcga 1320
taatgacgtg gaaggaagtc cgtcatttga gtcgaaaacc gatatcgtca tcattgtgaa 1380
cgacgtgaat gatcaggcgc cggtgccttt ccgtccgtca tacttcattg aaatcatgga 1440
ggaaactgcg atgacactta atttggaaga ctttggtttc cacgatagag atcttggtcc 1500
gcacgcgcag tacacagtgc acctggagag catccacccg gcgggagcgc acgaggcgtt 1560
ctacatcgcg ccggaggtgg gctaccagcg acagtccttc atcgtcggca cgcagaacca 1620
tcacatgctc gacttcgaag tgccagagtt ccagaagata caacttaggg tggtagccat 1680
agacatggac gatccgaggt gggttggtat cgcgattata aacattaacc tgatcaactg 1740
gaacgatgag ctgccgatct tcgagcacga tgtgcagact gtcaccttca aggagacgga 1800
gggcgctggc ttccgtgtcg ccactgtact ggctaaggac cgggatattg atgatagagt 1860
cgaacactct ctaatgggca acgcagtcaa ctacctgagt atcgacaaag acaccggcga 1920
catcctcgtg acaatcgacg atgcattcaa ctatcacaga caaaacgagc tctttgtgca 1980
gatacgagct gacgacacgc tgggagagcc gtacaacacc aacactgcct gttccggact 2040
gtcacatcgc gccggcctat gaggtcgcgc cagcacacgt catcgtgcgc cccacctaag 2100
ctgggccctc accatacgcc ggacccccgg acactcgctc agcgaccccg gtcgcgcata 2160

-continued

```
cacgaccgca cgggcaacgc gcgattttct cttgtacata cttcaataca gtcttctttg    2220
caaatcgaag tttcattgaa ccgccgagac catcatccta catctggacc tcggcgctca    2280
agcattggtc cctcgcaaga actgaaccga acaggagaag tcgtcttgca agctgcgcaa    2340
ccgcccgtgg actttggact ggtcacccgc ctctgcgact tacgcgtcgt catcgcatcg    2400
tggaggacta gtgggacgt gtctacccgg aaggaaggaa catactgagt gagtccgttc     2460
cgatatccct ttgaattcct gtcgttattc ccttgtatcc aggaatccag gaatttaaag    2520
ggcttcttac attgatcagg catattgatc tcttcataca tcttatttct tacgcttacg    2580
tactaaattc ataaatctat aaacttttgc acataagttc gttatctttt aaacagtaga    2640
ttctttgttc atttgcatta cgtaaacaag ctcattagcg agcggcttag cgaaccggtt    2700
tctaaacccg gtcgttcgct tcgaatcagc tgattcattg tcacttgcct atttaaacat    2760
tttatttcat atttaacgtt ttttctttg tttgtttatt ttattttatt ttcattcttc     2820
cacgtttgct ttcttgctta agtatggct gatgcaacgt tggaggaact tcttagaggg     2880
cgtggtaatt tcgaagccga gcttggacgt ttcgataact ttttaaattc gttaacaagt    2940
ccatatttag acagtgctca tatggctaca ttgcagtctc gaattagttt tatattggca    3000
ctttatgatg acttcgacat gtttcagacg gagttggagg tgttgtcgga gaacgtcgac    3060
gacatgttgg tcgagcggga gcgtatcgag tcgcggtact tcgcactggt ggcgcgtgcg    3120
aagttcaccc ttaaacacgg gcgtgcgtca tcacctgcgg tcttgcctgc acttcctgtt    3180
gaagacgtcc ggcagcacgg ctctgactgc gggcacggcc tggttcagct gccagagatg    3240
gacttgagct gcataccttc tgagaccagt accgggattc ttgcatctcg ggggtgaag     3300 gctgattcca tcagctcgtc cactctttgg cggtcaggtt gtacacagta cacaaccacg    3360
tcatcaaatt cagtacatac aacatctatt acgtatatta ataatgaatt ggcacacaac    3420
aacaacaatt ccatttcatt aataaaccaa aaaacatctg aaccacatgc agaatcatca    3480
cataacctca tattacagac cttctcatca cacataatat atcactcaaa tacatacttt    3540
acgatgccat gcatcaaaga tataccattg cctttgatac attggctgca ttacacgagc    3600
aaactacgtt acacattgtc aagcgttttg tgctctgcag ccggagccgt gcttctggag    3660
ctggtacccg tgtttcttgc gccttcagcc agttatccgg actgacgcgc gtactccgac    3720
aacagctgct tctttttct ttgcattttc cttttttcac ccttttcatg atgagatcac     3780
tttgctatgg tcaggttaga ggcttgctta aattccatac cttctccctc tacccatctg    3840
acctctctca tcttttccca gacacatcca tatcggacgg ccactcatgt gtacctttca    3900
ccggcagatc actaacccac ctcttctgtg gctgtcacca gtgactactg cctccatcaa    3960
cgcagaccag agaggcgtca ccacaccatc atcatcatca tcttgaagcc ttgacaggct    4020
tcaacccggg gaatatgttc cggactgtca catcgcgccg gcctatgagg tcgcgccagc    4080
acacgtcatc gtgcgcccca cctaagctgg gccctcacca tacgccggac ccccggacac    4140
tcgctcatcg accccggtcg cgcatacacg accgcacgcg caacgcgcga tctactcttg    4200
tcacctatct ataatacagt cttctacttt gaacatcgaa gttttattga aacgccgaga    4260
ccagcaacct acacctgcac ctcggcgctc aaacactgcc caactggtga tacagctgca    4320
agacatcaac aacacacctc ctacgctcag actgccccgc acgaccccgt cagtggaaga    4380
gaacgtgccg gacgggttcg tgatccccac cgagctgcac gcctccgacc ccgacaccac    4440
cgccgagctg cgcttcagca tcgactggga cacttcctac gccaccaagc agggcaggga    4500
```

```
tgctgatgct aaggagtttg ttaattgtat agaaatcgag acggtatacc cgaacttgaa   4560
cgaccgaggc accgccatcg gccgcgtggt ggttcgcgag atccgggaac acgtcactat   4620
agactacgag atgttcgggg tgctgtacct cacagtcagg gtcacggatc tcaacacggt   4680
cattggagac gactatgata tatcaacatt cacaatcata ataatagaca tgaacgacaa   4740
ccctccgctg tgggtggaag gcactctgac gcaggagttc cgcgtgcgag aggtcgccgc   4800
ctcaggagtt attataggat ccgtactcgc taccgatatc gacggacctc cttataatca   4860
agtgcggtat accatcactc ctagactgga cactccagaa gacctagtgg agatcgactt   4920
caattcgggt cagatctcag tgaagaagca ccaggctatc gacgcggacg agccgccgcg   4980
ccagcacctc tactacaccg tggtcgccag cgacaagtgc gacctgctct ctgtcgacgt   5040
gtgtccgcct gatcctaact acttcaacac gcccggagag ataacgatcc acataacaga   5100
cacgaacaat aaggtgcctc gagtggaaga ggacaagttc gaggaaactg tctatatcta   5160
cgagggcgcg gaggacggag aacacgtcgt gcaactcttc gccagcgatc tggatagaga   5220
tgaaatctac cacaaagtga gctaccagat caactacgcg atcaaccctc gtctccgcga   5280
cttcttcgag gtagacttgg agaccggcct ggtgtacgtc aacaacactg ccggggagaa   5340
actcgacaga gacggcgatg aacccacgca tcggatcttc ttcaacgtca tcgataactt   5400
ctatggagaa ggagatggca accggaatca ggacagagaca caagtgttgg tggtgctgtt   5460
ggacatcaac gacaactacc cggaactgcc tgagggtctc tcatgggata tctctgaggg   5520
cttgctacag ggtgtccgtg taaccccaga tatcttcgcc ccggaccgcg acgagcccgg   5580
caccgacaac tcccgcgtgg cgtacgacat cgtcagcctc acgcccaccg acagggacat   5640
cacacttcct caactcttca ccatgatcac catagagaag gacaggggca tcgaccagac   5700
tggagagctg gagaccgcta tggatttaag aggctattgg ggcacttatg aagtacatgt   5760
caaggcatac gaccatggag ttcctcaaag gatatcctac gagaagtacc cgctagttat   5820
aagaccttac aacctccacg accctgtgtt cgtgttccct caacctggaa tgactatcag   5880
actcgcggag gagcgagcag tagtgaacgg cgtgctggcg acagtggacg gcgagttcct   5940
cgagcgaatc gtcgccaccg acgaggatgg cttacacgct ggagttgtta ccttctctat   6000
ctctggagat gaggaggcgt tgcagtactt cgacgtgttt aacgacgag tgaacttagg   6060 tgcgctgacc atcacgcagc tcttccctga agacttccga gagtttcagg tgacgattcg   6120
tgctacggat ggtggtacgg agccaggtcc aagaagtacg gactgcacgg tcaccgtagt   6180
gtttgttcct acgcagggag agcctgtgtt cgagactagc acctacacgg tcgcttttat   6240
tgagaaagac gctggtatgg aagagcgggc cacgctgcct ctcgccaagg acccgcgtaa   6300
cataatgtgt gaagatgatt gtcacgcaca cttattacagc attgttggag gcaactcgat   6360
gggccacttc gcagtagacc cccagtccaa cgagctgttc ctgctgacgc cgctggagcg   6420
cgcggagcag gagacgcaca ccctcatcat cggcgccagc gactcgccca gcccggccgc   6480
cgtgctgcag gcttccaccc tcactgttac tgtcaatgtt cgagaagcaa acccgcggcc   6540
agtgttccag agcgctctgt acacagccgg catctccacc ctcgacacca tcaacagagc   6600
tctgctgacc ttacacgcga cccattcaga aggcctgccc gtgacctaca cgctgataca   6660
agactctatg gaagctgact ccacactgca agctgtgcag gagacagcct tcaacctgaa   6720
ccctcagact ggagtgctga ccctcaactt ccagcccaca gcatctatgc acggcatgtt   6780
tgagttcgat gtgatggcta ctgatacagt gggagagacc gcgcgcactg aagtgaaggt   6840
gtacctgata tccgaccgca acagagtgtt cttcacgttc atgaacacgc tcgaagaagt   6900
```

-continued

```
cgaaccgaat gaggatttca tagcggaaac atttaccctg tttttcggca tgcggtgcaa    6960
catcgaccag acgctgcccg ccagcgaccc cgccaccggc gccgccaggg acgaccagac    7020
cgaagtcagg gcacacttca tacgcgacga cctgcctgta ccggctgagg agattgaaca    7080
gttgcgcggt aatccaacac tagtggcgac aatccagaac gccctgcagg aggagaacct    7140
gaacctagcc gacctgttca cgggcgagac tcccatcctg gcggcgagg cgcaggcgcg     7200
ggcggtgtac gcgctggcgg cggtggcggc cgcgctcgcg ctgctctgtg tcgtactgct    7260
tatactcttc ttcatcagga ctagggccct caaccgtcgt ctggaagctc tctccatgac    7320
caagtacagt tcccaagact cgggtctgaa ccgcgtgggt ctggcggcgc cgggcaccaa    7380
caagcacgcg gtggagggct ccaacccaat ctggaacgaa accctcaagg caccggactt    7440
tgatgctctt agcgagcagt cgtacgactc ggatctgatc ggcatcgaag acttgccgca    7500
gttcaggaac gactacttcc cgcctgacga ggagagctcc atgcggggag tcgtcaatga    7560
acacatgcct ggagctaatt cagtagcaaa ccataacaat aacttcgggt tcaacgctac    7620
cccccttcagc ccagagttcg cgaactcgca gctcagaaga taaaatatta tagtattttt    7680
ttatataata ttatgtaaaa gtgatataac gcacactaaa atttacctat aagtatatat    7740
tgaagtgtaa gatactcgta ttatgtaaga gcatttatt ttttactacc agacagtaa     7799
```

<210> SEQ ID NO 4
<211> LENGTH: 2263
<212> TYPE: DNA
<213> ORGANISM: Heliothis virescens

<400> SEQUENCE: 4

```
tgttccggac tgtcacatcg cgccggccta tgaggtcgcg ccagcacacg tcatcgtgcg    60
ccccacctaa gctgggccct caccatacgc cggaccccg gacactcgct cagcgacccc     120
ggtcgcgcat acacgaccgc acgggcaacg cgcgattttc tcttgtacat acttcaatac    180
agtcttcttt gcaaatcgaa gtttcattga accgccgaga ccatcatcct acatctggac    240
ctcggcgctc aagcattggt ccctcgcaag aactgaaccg aacaggagaa gtcgtcttgc    300
aagctgcgca accgccgtg gactttggac tggtcacccg cctctgcgac ttacgcgtcg     360
tcatcgcatc gtggaggact agtggggacg tgtctacccg gaaggaagga acatactgag    420
tgagtccgtt ccgatatccc tttgaattcc tgtcgttatt cccttgtatc caggaatcca    480
ggaatttaaa gggcttctta cattgatcag gcatattgat ctcttcatac atcttatttc    540
ttacgcttac gtactaaatt cataaatcta taaacttttg cacataagtt cgttatcttt    600
taaacagtag attctttgtt catttgcatt acgtaaacaa gctcattagc gagcggctta    660
gcgaaccggt ttctaaaccc ggtcgttcgc ttcgaatcag ctgattcatt gtcacttgcc    720
tatttaaaca ttttatttca tatttaacgt ttttttcttt gtttgtttat tttatttat     780
tttcattctt ccacgtttgc tttcttgctt aaagtatggc tgatgcaacg ttggaggaac    840
ttcttagagg gcgtggtaat ttcgaagccg agcttgacg tttcgataac tttttaaatt     900
cgttaacaag tccatattta gacagtgctc atatggctac attgcagtct cgaattagtt    960
ttatattggc actttatgat gacttcgaca tgtttcagac ggagttggag tgttgtcgg     1020
agaacgtcga cgacatgttg gtcgagcggg agcgtatcga gtcgcggtac ttcgcactgg    1080
tggcgcgtgc gaagttcacc cttaaacacg ggcgtgcgtc atcacctgcg gtcttgcctg    1140
cacttcctgt tgaagacgtc cggcagcacg gctctgactg cgggcacggc ctggttcagc    1200
```

```
tgccagagat ggacttgagc tgcatacctt ctgagaccag taccgggatt cttgcatctc    1260 gggggtgaa ggctgattcc atcagctcgt ccactctttg gcggtcaggt tgtacacagt    1320
acacaaccac gtcatcaaat tcagtacata caacatctat tacgtatatt aataatgaat    1380
tggcacacaa caacaacaat tccatttcat taataaacca aaaaacatct gaaccacatg    1440
cagaatcatc acataacctc atattacaga ccttctcatc acacataata tatcactcaa    1500
atacatactt tacgatgcca tgcatcaaag atataccatt gcctttgata cattggctgc    1560
attacacgag caaactacgt tacacattgt caagcgtttt gtgctctgca gccggagccg    1620
tgcttctgga gctggtaccc gtgtttcttg cgccttcagc cagttatccg gactgacgcg    1680
cgtactccga caacagctgc ttcttttttc tttgcatttt ccttttttca ccctttcat    1740 gatgagatca ctttgctatg gtcaggttag aggcttgctt aaattccata ccttctccct    1800
ctacccatct gacctctctc atcttttccc agacacatcc atatcggacg ccactcatg    1860 tgtacctttc accggcagat cactaaccca cctcttctgt ggctgtcacc agtgactact    1920
gcctccatca acgcagacca gagaggcgtc accacaccat catcatcatc atcttgaagc    1980
cttgacaggc ttcaacccgg ggaatatgtt ccggactgtc acatcgcgcc ggcctatgag    2040
gtcgcgccag cacacgtcat cgtgcgcccc acctaagctg ggccctcacc atacgccgga    2100
cccccggaca ctcgctcatc gaccccggtc gcgcatacac gaccgcacgc gcaacgcgcg    2160
atctactctt gtcacctatc tataatacag tcttctactt tgaacatcga agttttattg    2220
aaacgccgag accagcaacc tacacctgca cctcggcgct caa                      2263

<210> SEQ ID NO 5
<211> LENGTH: 252
<212> TYPE: DNA
<213> ORGANISM: Heliothis virescens

<400> SEQUENCE: 5
tgttccggac tgtcacatcg cgccggccta tgaggtcgcg ccagcacacg tcatcgtgcg     60
cccccaccta agctgggccct caccatacgc cggaccccccg gacactcgct cagcgacccc   120
ggtcgcgcat acacgaccgc acgggcaacg cgcgattttc tcttgtacat acttcaatac   180
agtcttcttt gcaaatcgaa gtttcattga accgccgaga ccatcatcct acatctggac   240
ctcggcgctc aa                                                         252

<210> SEQ ID NO 6
<211> LENGTH: 257
<212> TYPE: DNA
<213> ORGANISM: Heliothis virescens

<400> SEQUENCE: 6
tgttccggac tgtcacatcg cgccggccta tgaggtcgcg ccagcacacg tcatcgtgcg     60
cccccaccta agctgggccct caccatacgc cggaccccccg gacactcgct catcgacccc   120
ggtcgcgcat acacgaccgc acgcgcaacg cgcgatctac tcttgtcacc tatctataat   180
acagtcttct actttgaaca tcgaagtttt attgaaacgc cgagaccagc aacctacacc   240
tgcacctcgg cgctcaa                                                    257

<210> SEQ ID NO 7
<211> LENGTH: 26
<212> TYPE: DNA
<213> ORGANISM: Heliothis virescens

<400> SEQUENCE: 7
```

-continued

```
atacgagctg acgacacgct gggaga                                                  26

<210> SEQ ID NO 8
<211> LENGTH: 30
<212> TYPE: DNA
<213> ORGANISM: Heliothis virescens

<400> SEQUENCE: 8
tctgagcgta ggaggtgtgt tgttgatgtc                                              30

<210> SEQ ID NO 9
<211> LENGTH: 24
<212> TYPE: DNA
<213> ORGANISM: Heliothis virescens

<400> SEQUENCE: 9
gcgcgatgtg acagtccgga acag                                                    24

<210> SEQ ID NO 10
<211> LENGTH: 622
<212> TYPE: PRT
<213> ORGANISM: Heliothis virescens

<400> SEQUENCE: 10

Met Ala Val Asp Val Arg Met Leu Thr Ala Val Leu Ile Leu Ala
 1               5                  10                  15

Ala Asn Leu Thr Phe Ala Gln Asp Cys Ser Tyr Met Val Ala Ile Pro
                20                  25                  30

Arg Pro Glu Arg Pro Asp Phe Pro Asn Gln Asn Phe Glu Gly Val Pro
            35                  40                  45

Trp Ser Gln Asn Pro Leu Leu Pro Ala Glu Asp Arg Glu Asp Val Cys
        50                  55                  60

Met Asn Ala Phe Asp Pro Ser Ala Leu Asn Pro Val Thr Val Ile Phe
 65                  70                  75                  80

Met Glu Glu Ile Glu Gly Asp Val Ala Ile Ala Arg Leu Asn Tyr
                85                  90                  95

Arg Gly Thr Asn Thr Pro Thr Val Val Thr Pro Phe Asn Phe Gly Thr
            100                 105                 110

Phe His Leu Leu Gly Pro Val Ile Arg Arg Ile Pro Glu Gln Gly Gly
        115                 120                 125

Asp Trp His Leu Val Ile Thr Gln Arg Gln Asp Tyr Glu Thr Pro Asn
    130                 135                 140

Met Gln Gln Tyr Ile Phe Asn Val Arg Val Glu Asp Glu Pro Gln Glu
145                 150                 155                 160

Ala Thr Val Met Leu Ile Ile Val Asn Ile Asp Asp Asn Ala Pro Ile
                165                 170                 175

Ile Gln Met Phe Glu Pro Cys Asp Ile Pro Glu His Gly Glu Thr Gly
            180                 185                 190

Thr Thr Glu Cys Lys Tyr Val Val Ser Asp Ala Asp Gly Glu Ile Ser
        195                 200                 205

Thr Arg Phe Met Thr Phe Glu Ile Glu Ser Asp Arg Asn Asp Glu Glu
    210                 215                 220

Tyr Phe Glu Leu Val Arg Glu Asn Ile Gln Gly Gln Trp Met Tyr Val
225                 230                 235                 240

His Met Arg Leu Ile Leu Asn Lys Pro Leu Asp Tyr Glu Glu Asn Pro
                245                 250                 255
```

```
Leu His Leu Phe Arg Val Thr Ala Leu Asp Ser Leu Pro Asn Ile His
            260                 265                 270

Thr Val Thr Met Met Val Gln Val Glu Asn Ile Glu Ser Arg Pro Pro
        275                 280                 285

Arg Trp Met Glu Ile Phe Ala Val Gln Gln Phe Asp Glu Lys Thr Ala
    290                 295                 300

Gln Ser Phe Arg Val Arg Ala Ile Asp Gly Asp Thr Gly Ile Asp Lys
305                 310                 315                 320

Pro Ile Phe Tyr Arg Ile Glu Thr Glu Glu Ser Glu Lys Asp Leu Phe
                325                 330                 335

Ser Val Glu Thr Ile Gly Ala Gly Arg Glu Gly Ala Trp Phe Lys Val
            340                 345                 350

Ala Pro Ile Asp Arg Asp Thr Leu Glu Lys Glu Val Phe His Val Ser
        355                 360                 365

Leu Ile Ala Tyr Lys Tyr Gly Asp Asn Asp Val Glu Gly Ser Pro Ser
    370                 375                 380

Phe Glu Ser Lys Thr Asp Ile Val Ile Val Asn Asp Val Asn Asp
385                 390                 395                 400

Gln Ala Pro Val Pro Phe Arg Pro Ser Tyr Phe Ile Glu Ile Met Glu
                405                 410                 415

Glu Thr Ala Met Thr Leu Asn Leu Glu Asp Phe Gly Phe His Asp Arg
            420                 425                 430

Asp Leu Gly Pro His Ala Gln Tyr Thr Val His Leu Glu Ser Ile His
        435                 440                 445

Pro Ala Gly Ala His Glu Ala Phe Tyr Ile Ala Pro Glu Val Gly Tyr
    450                 455                 460

Gln Arg Gln Ser Phe Ile Val Gly Thr Gln Asn His His Met Leu Asp
465                 470                 475                 480

Phe Glu Val Pro Glu Phe Gln Lys Ile Gln Leu Arg Val Val Ala Ile
                485                 490                 495

Asp Met Asp Asp Pro Arg Trp Val Gly Ile Ala Ile Asn Ile Asn
            500                 505                 510

Leu Ile Asn Trp Asn Asp Glu Leu Pro Ile Phe Glu His Asp Val Gln
        515                 520                 525

Thr Ala Thr Phe Lys Glu Thr Glu Gly Ala Gly Phe Arg Val Ala Thr
    530                 535                 540

Val Leu Ala Lys Asp Arg Asp Ile Asp Glu Arg Val Glu His Ser Leu
545                 550                 555                 560

Met Gly Asn Ala Val Asn Tyr Leu Ser Ile Asp Lys Asp Thr Gly Asp
                565                 570                 575

Ile Leu Val Thr Ile Asp Asp Ala Phe Asn Tyr His Arg Gln Asn Glu
            580                 585                 590

Leu Phe Val Gln Ile Arg Ala Asp Asp Thr Leu Glu Glu Pro Tyr Asn
        595                 600                 605

Ala Asn Thr Ala Cys Ser Gly Leu Ser His Arg Ala Gly Leu
    610                 615                 620

<210> SEQ ID NO 11
<211> LENGTH: 1714
<212> TYPE: PRT
<213> ORGANISM: Bombyx mori

<400> SEQUENCE: 11

Met Gly Val Asp Val Arg Ile Leu Ala Thr Leu Leu Leu Ile Tyr Ala
 1               5                  10                  15
```

```
Glu Thr Val Leu Ala Gln Glu Arg Cys Gly Phe Met Val Ala Ile Pro
         20                  25                  30

Arg Pro Pro Arg Pro Asp Leu Pro Glu Leu Asp Phe Glu Gly Gln Thr
             35                  40                  45

Trp Ser Gln Arg Pro Leu Ile Pro Ala Ala Asp Arg Glu Asp Val Cys
         50                  55                  60

Met Asp Gly Tyr His Ala Met Thr Pro Thr Tyr Gly Thr Gln Ile Ile
 65                  70                  75                  80

Tyr Met Glu Glu Glu Ile Glu Gly Val Pro Ile Ala Lys Leu Asn
             85                  90                  95

Tyr Arg Gly Pro Asn Val Pro Tyr Ile Glu Pro Ala Phe Leu Ser Gly
             100                 105                 110

Ser Phe Asn Leu Leu Val Pro Val Ile Arg Arg Ile Pro Asp Ser Asn
             115                 120                 125

Gly Glu Trp His Leu Ile Ile Thr Gln Arg Gln Asp Tyr Glu Thr Pro
     130                 135                 140

Gly Met Gln Gln Tyr Val Phe Asn Ile Arg Ile Asp Gly Glu Thr Leu
145                 150                 155                 160

Val Ala Gly Val Ser Leu Leu Ile Val Asn Ile Asp Asp Asn Ala Pro
                 165                 170                 175

Ile Ile Gln Ala Leu Glu Pro Cys Gln Val Asp Glu Leu Gly Glu Ala
             180                 185                 190

Arg Leu Thr Glu Cys Val Tyr Val Val Thr Asp Ala Asp Gly Arg Ile
     195                 200                 205

Ser Thr Gln Phe Met Gln Phe Arg Ile Asp Ser Asp Arg Gly Asp Asp
     210                 215                 220

Lys Ile Phe Tyr Ile Gln Gly Ala Asn Ile Pro Gly Glu Trp Ile Arg
225                 230                 235                 240

Met Thr Met Thr Val Gly Ile Asn Glu Pro Leu Asn Phe Glu Thr Asn
                 245                 250                 255

Pro Leu His Ile Phe Ser Val Thr Ala Leu Asp Ser Leu Pro Asn Thr
             260                 265                 270

His Thr Val Thr Leu Met Val Gln Val Glu Asn Val Glu His Arg Pro
     275                 280                 285

Pro Arg Trp Val Glu Ile Phe Ala Val Gln Gln Phe Asp Glu Lys Thr
     290                 295                 300

Ala Gln Ser Phe Pro Val Arg Ala Ile Asp Gly Asp Thr Gly Ile Asn
305                 310                 315                 320

Lys Pro Ile His Tyr Arg Leu Glu Thr Ala Glu Asp Thr Phe Phe
                 325                 330                 335

His Ile Arg Thr Ile Glu Gly Gly Arg Ser Gly Ala Ile Leu Tyr Val
             340                 345                 350

Asp Pro Ile Asp Arg Asp Thr Leu Gln Arg Glu Val Phe Gln Leu Ser
             355                 360                 365

Ile Ile Ala Tyr Lys Tyr Asp Asn Glu Ser Ser Ala Thr Ala Ala Asn
     370                 375                 380

Val Val Ile Ile Val Asn Asp Ile Asn Asp Gln Arg Pro Glu Pro Leu
385                 390                 395                 400

Phe Lys Glu Tyr Arg Leu Asn Ile Met Glu Glu Thr Ala Leu Thr Leu
                 405                 410                 415

Asn Phe Asp Gln Glu Phe Gly Phe His Asp Arg Asp Leu Gly Gln Asn
             420                 425                 430
```

```
Ala Gln Tyr Thr Val Arg Leu Glu Ser Asp Tyr Pro Ala Asp Ala Ala
        435                 440                 445

Lys Ala Phe Tyr Ile Ala Pro Glu Val Gly Tyr Gln Arg Gln Thr Phe
        450                 455                 460

Ile Met Gly Thr Ala Asn His Lys Met Leu Asp Tyr Glu Val Pro Glu
465                 470                 475                 480

Phe Gln Arg Ile Arg Leu Arg Val Ile Ala Thr Asp Met Asp Asn Glu
                485                 490                 495

Glu His Val Gly Val Ala Tyr Val Tyr Ile Asn Leu Ile Asn Trp Asn
                500                 505                 510

Asp Glu Glu Pro Ile Phe Glu His Ser Val Gln Asn Val Ser Phe Lys
            515                 520                 525

Glu Thr Glu Gly Lys Gly Phe Phe Val Ala Asn Val Arg Ala His Asp
            530                 535                 540

Arg Asp Ile Asp Asp Arg Val Glu His Thr Leu Met Gly Asn Ala Asn
545                 550                 555                 560

Asn Tyr Leu Ser Ile Asp Lys Asp Thr Gly Asp Ile His Val Thr Gln
                565                 570                 575

Asp Asp Phe Phe Asp Tyr His Arg Gln Ser Glu Leu Phe Val Gln Val
            580                 585                 590

Arg Ala Asp Asp Thr Leu Gly Glu Pro Phe His Thr Ala Thr Ser Gln
            595                 600                 605

Leu Leu Ile His Leu Glu Asp Ile Asn Asn Thr Pro Pro Thr Leu Arg
        610                 615                 620

Leu Pro Arg Gly Ser Pro Asn Val Glu Glu Asn Val Pro Glu Gly Tyr
625                 630                 635                 640

Ile Ile Thr Ser Glu Ile Arg Ala Thr Asp Pro Asp Thr Thr Ala Glu
                645                 650                 655

Leu Arg Phe Glu Ile Asp Trp Thr Thr Ser Tyr Ala Thr Lys Gln Gly
                660                 665                 670

Arg Glu Ala Asn Pro Ile Glu Phe His Asn Cys Val Glu Ile Glu Thr
            675                 680                 685

Ile Tyr Pro Ala Ile Asn Asn Arg Gly Ser Ala Ile Gly Arg Leu Val
        690                 695                 700

Val Lys Lys Ile Arg Glu Asn Val Thr Ile Asp Tyr Glu Glu Phe Glu
705                 710                 715                 720

Met Leu Tyr Leu Thr Val Arg Val Arg Asp Leu Asn Thr Val Ile Gly
                725                 730                 735

Asp Asp Tyr Asp Glu Ser Thr Phe Thr Ile Thr Ile Asp Met Asn
                740                 745                 750

Asp Asn Pro Pro Ile Trp Val Pro Gly Thr Leu Glu Gln Ser Leu Arg
        755                 760                 765

Val Arg Glu Met Ser Asp Ala Gly Val Val Ile Gly Thr Leu Thr Ala
770                 775                 780

Thr Asp Ile Asp Gly Pro Leu Tyr Asn Gln Val Arg Tyr Thr Met Lys
785                 790                 795                 800

Ala Asn Glu Gly Thr Pro Glu Asn Leu Leu Met Ile Asp Phe Tyr Thr
                805                 810                 815

Gly Gln Ile Thr Val Lys Thr Ser Gly Ala Ile Asp Ala Asp Val Pro
            820                 825                 830

Arg Arg Tyr Asn Leu Tyr Tyr Thr Val Val Ala Thr Asp Arg Cys Tyr
        835                 840                 845

Ala Glu Asp Pro Asp Asp Cys Pro Asp Asp Pro Thr Tyr Trp Glu Thr
```

-continued

```
            850                 855                 860
Pro Gly Gln Val Val Ile Gln Ile Ile Asp Thr Asn Asn Lys Ile Pro
865                 870                 875                 880

Gln Pro Glu Thr Asp Gln Phe Lys Ala Val Val Tyr Ile Tyr Glu Asp
                    885                 890                 895

Ala Val Ser Gly Asp Glu Val Val Lys Val Ile Gly Ser Asp Leu Asp
                900                 905                 910

Arg Asp Asp Ile Tyr His Thr Ile Arg Tyr Gln Ile Asn Tyr Ala Val
                915                 920                 925

Asn Pro Arg Leu Arg Asp Phe Phe Ala Val Asp Pro Asp Thr Gly Arg
930                 935                 940

Val Tyr Val Tyr Tyr Thr Thr Asp Glu Val Leu Asp Arg Asp Gly Asp
945                 950                 955                 960

Glu Pro Gln His Arg Ile Phe Phe Asn Leu Ile Asp Asn Phe Phe Gln
                965                 970                 975

Gln Gly Asp Gly Asn Arg Asn Gln Asn Asp Ala Glu Val Leu Val Val
                980                 985                 990

Leu Leu Asp Val Asn Asp Asn Ala Pro Glu Leu Pro Glu Pro Asp Glu
                995                 1000                1005

Leu Ser Trp Ser Val Ser Glu Ser Leu Thr Lys Gly Thr Arg Leu Gln
                1010                1015                1020

Pro His Ile Tyr Ala Pro Asp Arg Asp Glu Pro Asp Thr Asp Asn Ser
1025                1030                1035                1040

Arg Val Gly Tyr Ala Ile Ile Ser Leu Thr Ile Ala Asn Arg Glu Ile
                1045                1050                1055

Glu Val Pro Glu Leu Phe Thr Met Ile Gln Ile Gln Asn Val Thr Gly
                1060                1065                1070

Glu Leu Glu Thr Ala Met Asp Leu Arg Gly Tyr Trp Gly Thr Tyr Ala
                1075                1080                1085

Ile His Ile Lys Ala Tyr Asp His Gly Ile Pro Gln Gln Met Ser Asn
                1090                1095                1100

Glu Thr Tyr Glu Leu Val Ile Arg Pro Tyr Asn Phe His Ala Pro Val
1105                1110                1115                1120

Phe Val Phe Pro Lys His Gly Ala Thr Leu Arg Leu Ala Arg Glu Arg
                1125                1130                1135

Ala Val Val Asn Gly Leu Ala Thr Val Asp Gly Glu Phe Leu Asn Arg
                1140                1145                1150

Ile Val Ala Thr Asp Glu Asp Gly Leu His Ala Gly Gln Val Ala Phe
                1155                1160                1165

Glu Val Val Gly Asp Thr Glu Ala Val Asp Tyr Phe His Ile Val Asn
                1170                1175                1180

Asp Gly Glu Asn Ser Gly Thr Leu Met Leu Lys Gln Leu Phe Pro Glu
1185                1190                1195                1200

Asp Ile Arg Glu Phe Glu Val Thr Ile Arg Ala Thr Asp Gly Gly Thr
                    1205                1210                1215

Glu Pro Arg Pro Leu Ser Thr Asp Cys Thr Phe Ser Val Val Phe Val
                    1220                1225                1230

Pro Ile Gln Gly Glu Pro Ile Phe Pro Thr Ser Thr His Thr Val Ala
                    1235                1240                1245

Phe Ile Glu Lys Glu Ala Gly Leu Leu Glu Arg His Glu Leu Pro Arg
1250                1255                1260

Ala Glu Asp Arg Lys Asn His Leu Cys Ser Asp Asp Cys His Asn Ile
1265                1270                1275                1280
```

```
Tyr Tyr Arg Ile Ile Asp Gly Asn Asn Asp Gly His Phe Gly Leu Asp
            1285                1290                1295
Glu Thr Thr Asn Val Leu Phe Leu Val Lys Glu Leu Asp Arg Ser Val
        1300                1305                1310
Ser Glu Thr Tyr Thr Leu Thr Ile Ala Ala Ser Asn Ser Pro Thr Gly
        1315                1320                1325
Gly Ile Ala Leu Thr Ser Thr Ile Thr Ile Thr Val Asn Val Arg Glu
        1330                1335                1340
Ala Asp Pro Gln Pro Tyr Phe Val Arg Asp Leu Tyr Thr Ala Gly Ile
1345                1350                1355                1360
Ser Thr Ser Asp Ser Ile Asn Arg Glu Leu Leu Ile Leu Gln Ala Thr
            1365                1370                1375
His Ser Glu Asn Ala Pro Ile Ile Tyr Thr Ile Asp Trp Ser Thr Met
            1380                1385                1390
Val Thr Asp Pro Thr Leu Ala Ser Val Arg Glu Thr Ala Phe Ile Leu
            1395                1400                1405
Asn Pro His Thr Gly Val Leu Thr Leu Asn Ile Gln Pro Thr Ala Ser
    1410                1415                1420
Met His Gly Met Phe Glu Phe Gln Val Val Ala Thr Asp Pro Ala Gly
1425                1430                1435                1440
Tyr Ser Asp Arg Ala Asn Val Lys Ile Tyr Leu Ile Ser Thr Arg Asn
            1445                1450                1455
Arg Val Phe Phe Leu Phe Val Asn Thr Leu Glu Gln Val Glu Gln Asn
            1460                1465                1470
Thr Asp Phe Ile Ala Gln Thr Phe Ser Ala Gly Phe Glu Met Thr Cys
        1475                1480                1485
Asn Ile Asp Gln Val Val Pro Ala Thr Asp Ala Ser Gly Val Ile Met
    1490                1495                1500
Asn Gly Ile Thr Glu Val Arg Gly His Phe Ile Arg Asp Asn Val Pro
1505                1510                1515                1520
Val Pro Ala Asp Glu Ile Glu Thr Leu Arg Gly Asp Met Val Leu Leu
            1525                1530                1535
Thr Ala Ile Gln Ser Thr Leu Ala Thr Arg Leu Leu Val Leu Arg Asp
        1540                1545                1550
Leu Phe Thr Asp Thr Ser Pro Ala Pro Asp Ala Gly Ser Ala Ala Val
        1555                1560                1565
Leu Tyr Ala Leu Ala Val Leu Ser Ala Leu Leu Ala Ala Leu Cys Leu
        1570                1575                1580
Leu Leu Leu Val Ile Phe Ile Ile Arg Thr Lys Lys Leu Asn Arg Arg
1585                1590                1595                1600
Leu Glu Ala Leu Thr Val Lys Lys Tyr Gly Ser Val Asp Ser Gly Leu
            1605                1610                1615
Asn Arg Val Gly Ile Ala Ala Pro Gly Thr Asn Lys His Ala Val Glu
            1620                1625                1630
Gly Ser Asn Pro Ile Trp Asn Glu Thr Ile Lys Ala Pro Asp Phe Asp
        1635                1640                1645
Ser Met Ser Asp Ala Ser Asn Asp Ser Asp Leu Ile Gly Ile Glu Asp
        1650                1655                1660
Leu Pro His Phe Gly Glu Asn Asn Tyr Phe Pro Arg Asp Val Asp Glu
1665                1670                1675                1680
Phe Lys Thr Asp Lys Pro Glu Asp Ile Val Ala Thr His Asn Asn Asn
        1685                1690                1695
```

-continued

```
Phe Gly Phe Lys Ser Thr Pro Phe Ser Pro Glu Phe Ala Asn Gln Phe
            1700                1705                1710
Gln Lys

<210> SEQ ID NO 12
<211> LENGTH: 1527
<212> TYPE: PRT
<213> ORGANISM: Manduca sexta

<400> SEQUENCE: 12

Met Ala Val Asp Val Arg Ile Ala Ala Phe Leu Leu Val Phe Ile Ala
 1               5                  10                  15

Pro Ala Val Leu Ala Gln Glu Arg Cys Gly Tyr Met Thr Ala Ile Pro
             20                  25                  30

Arg Leu Pro Arg Pro Asp Asn Leu Pro Val Leu Asn Phe Glu Gly Gln
         35                  40                  45

Thr Trp Ser Gln Arg Pro Leu Leu Pro Ala Pro Glu Arg Asp Asp Leu
     50                  55                  60

Cys Met Asp Ala Tyr His Val Ile Thr Ala Asn Leu Gly Thr Gln Val
 65                  70                  75                  80

Ile Tyr Met Asp Glu Glu Ile Glu Asp Glu Ile Thr Ile Ala Ile Leu
                 85                  90                  95

Asn Tyr Asn Gly Pro Ser Thr Pro Phe Ile Glu Leu Pro Phe Leu Ser
            100                 105                 110

Gly Ser Tyr Asn Leu Leu Met Pro Val Ile Arg Arg Val Asp Asn Gly
        115                 120                 125

Ser Ala Ser His His Ala Arg Gln His Tyr Glu Leu Pro Gly Met
    130                 135                 140

Gln Gln Tyr Met Phe Asn Val Arg Val Asp Gly Gln Ser Leu Val Ala
145                 150                 155                 160

Gly Val Ser Leu Ala Ile Val Asn Ile Asp Asp Asn Ala Pro Ile Ile
                165                 170                 175

Gln Asn Phe Glu Pro Cys Arg Val Pro Glu Leu Gly Glu Pro Gly Leu
            180                 185                 190

Thr Glu Cys Thr Tyr Gln Val Ser Asp Ala Asp Gly Arg Ile Ser Thr
        195                 200                 205

Glu Phe Met Thr Phe Arg Ile Asp Ser Val Arg Gly Asp Glu Glu Thr
    210                 215                 220

Phe Tyr Ile Glu Arg Thr Asn Ile Pro Asn Gln Trp Met Trp Leu Asn
225                 230                 235                 240

Met Thr Ile Gly Val Asn Thr Ser Leu Asn Phe Val Thr Ser Pro Leu
                245                 250                 255

His Ile Phe Ser Val Thr Ala Leu Asp Ser Leu Pro Asn Thr His Thr
            260                 265                 270

Val Thr Met Met Val Gln Val Ala Asn Val Asn Ser Arg Pro Pro Arg
        275                 280                 285

Trp Leu Glu Ile Phe Ala Val Gln Gln Phe Glu Glu Lys Ser Tyr Gln
    290                 295                 300

Asn Phe Thr Val Arg Ala Ile Asp Gly Asp Thr Glu Ile Asn Met Pro
305                 310                 315                 320

Ile Asn Tyr Arg Leu Ile Thr Asn Glu Glu Asp Thr Phe Ser Ile Glu
                325                 330                 335

Ala Leu Pro Gly Gly Lys Ser Gly Ala Val Phe Leu Val Ser Pro Ile
            340                 345                 350
```

```
Asp Arg Asp Thr Leu Gln Arg Glu Val Phe Pro Leu Thr Ile Val Ala
        355                 360                 365
Tyr Lys Tyr Asp Glu Glu Ala Phe Ser Thr Ser Thr Asn Val Val Ile
        370                 375                 380
Ile Val Thr Asp Ile Asn Asp Gln Arg Pro Glu Pro Ile His Lys Glu
385                 390                 395                 400
Tyr Arg Leu Ala Ile Met Glu Glu Thr Pro Leu Thr Leu Asn Phe Asp
                405                 410                 415
Lys Glu Phe Gly Phe His Asp Lys Asp Leu Gly Gln Asn Ala Gln Tyr
            420                 425                 430
Thr Val Arg Leu Glu Ser Val Asp Pro Gly Ala Ala Glu Ala Phe
        435                 440                 445
Tyr Ile Ala Pro Glu Val Gly Tyr Gln Arg Gln Thr Phe Ile Met Gly
        450                 455                 460
Thr Leu Asn His Ser Met Leu Asp Tyr Glu Val Pro Glu Phe Gln Ser
465                 470                 475                 480
Ile Thr Ile Arg Val Val Ala Thr Asp Asn Asn Asp Thr Arg His Val
                485                 490                 495
Gly Val Ala Leu Val His Ile Asp Leu Ile Asn Trp Asn Asp Glu Gln
            500                 505                 510
Pro Ile Phe Glu His Ala Val Gln Thr Val Thr Phe Asp Glu Thr Glu
        515                 520                 525
Gly Glu Gly Phe Phe Val Ala Lys Ala Val Ala His Asp Arg Asp Ile
        530                 535                 540
Gly Asp Val Val Glu His Thr Leu Leu Gly Asn Ala Val Asn Phe Leu
545                 550                 555                 560
Thr Ile Asp Lys Leu Thr Gly Asp Ile Arg Val Ser Ala Asn Asp Ser
                565                 570                 575
Phe Asn Tyr His Arg Glu Ser Glu Leu Phe Val Gln Val Arg Ala Thr
            580                 585                 590
Asp Thr Leu Gly Gln Pro Phe His Thr Ala Thr Ser Gln Leu Val Ile
        595                 600                 605
Arg Leu Asn Asp Ile Asn Asn Thr Pro Pro Thr Leu Arg Leu Pro Arg
        610                 615                 620
Gly Ser Pro Gln Val Glu Glu Asn Val Pro Asp Ala His Val Ile Thr
625                 630                 635                 640
Gln Glu Leu Arg Ala Thr Asp Pro Asp Thr Thr Ala Asp Leu Arg Phe
                645                 650                 655
Glu Ile Asn Trp Asp Thr Ser Phe Ala Thr Lys Gln Gly Arg Gln Ala
            660                 665                 670
Asn Pro Asp Glu Phe Arg Asn Cys Val Glu Ile Glu Thr Ile Phe Pro
        675                 680                 685
Glu Ile Asn Asn Arg Gly Leu Ala Ile Gly Arg Val Val Ala Arg Glu
        690                 695                 700
Ile Arg His Asn Val Thr Ile Asp Tyr Glu Glu Phe Glu Val Leu Ser
705                 710                 715                 720
Leu Thr Val Arg Val Arg Asp Leu Asn Thr Val Tyr Gly Asp Asp Tyr
                725                 730                 735
Asp Glu Ser Met Leu Thr Ile Thr Ile Ile Asp Met Asn Asp Asn Ala
            740                 745                 750
Pro Val Trp Val Glu Gly Thr Leu Glu Gln Asn Phe Arg Val Arg Glu
        755                 760                 765
Met Ser Ala Gly Gly Leu Val Val Gly Ser Val Arg Ala Asp Asp Ile
```

-continued

```
            770                 775                 780
Asp Gly Pro Leu Tyr Asn Gln Val Arg Tyr Thr Ile Phe Pro Arg Glu
785                 790                 795                 800
Asp Thr Asp Lys Asp Leu Ile Met Ile Glu Leu Pro His Gly Ser Asn
                805                 810                 815
Phe Arg Glu His Lys Arg Arg Ile Asp Ala Asn Thr Pro Arg Phe
                820                 825                 830
His Leu Tyr Tyr Thr Val Val Ala Ser Asp Arg Cys Ser Thr Glu Asp
                835                 840                 845
Pro Ala Asp Cys Pro Pro Asp Pro Thr Tyr Trp Glu Thr Gly Asn
850                 855                 860
Ile Thr Ile His Ile Thr Asp Thr Asn Asn Lys Val Pro Gln Ala Glu
865                 870                 875                 880
Thr Thr Lys Phe Asp Thr Val Tyr Ile Tyr Glu Asn Ala Thr His
                885                 890                 895
Leu Asp Glu Val Val Thr Leu Ile Ala Ser Asp Leu Asp Arg Asp Glu
                900                 905                 910
Ile Tyr His Met Val Ser Tyr Val Ile Asn Tyr Ala Val Asn Pro Arg
                915                 920                 925
Leu Met Asn Phe Phe Ser Val Asn Arg Glu Thr Gly Leu Val Tyr Val
                930                 935                 940
Asp Tyr Glu Thr Gln Gly Ser Gly Glu Val Leu Asp Arg Asp Gly Asp
945                 950                 955                 960
Glu Pro Thr His Arg Ile Phe Phe Asn Leu Ile Asp Asn Phe Met Gly
                965                 970                 975
Glu Gly Glu Gly Asn Arg Asn Gln Asn Asp Thr Glu Val Leu Val Ile
                980                 985                 990
Leu Leu Asp Val Asn Asp Asn Ala Pro Glu Leu Pro Pro Ser Glu
                995                 1000                1005
Leu Ser Trp Thr Ile Ser Glu Asn Leu Lys Gln Gly Val Arg Leu Glu
       1010                1015                1020
Pro His Ile Phe Ala Pro Asp Arg Asp Glu Pro Asp Thr Asp Asn Ser
1025                1030                1035                1040
Arg Val Gly Tyr Glu Ile Leu Asn Leu Ser Thr Glu Arg Asp Ile Glu
                1045                1050                1055
Val Pro Glu Leu Phe Val Met Ile Gln Ile Ala Asn Val Thr Gly Glu
                1060                1065                1070
Leu Glu Thr Ala Met Asp Leu Lys Gly Tyr Trp Gly Thr Tyr Ala Ile
       1075                1080                1085
Tyr Ile Leu Ala Phe Asp His Gly Ile Pro Gln Met Ser Met Asn Glu
       1090                1095                1100
Thr Tyr Glu Leu Ile Ile His Pro Phe Asn Tyr Tyr Ala Pro Glu Phe
1105                1110                1115                1120
Val Phe Pro Thr Asn Asp Ala Val Ile Arg Leu Ala Arg Glu Arg Ala
                1125                1130                1135
Val Ile Asn Gly Val Leu Ala Thr Val Asn Gly Glu Phe Leu Glu Arg
                1140                1145                1150
Ile Ser Ala Thr Asp Pro Asp Gly Leu His Ala Gly Val Val Thr Phe
       1155                1160                1165
Gln Val Val Gly Asp Glu Glu Ser Gln Arg Tyr Phe Gln Val Val Asn
       1170                1175                1180
Asp Gly Glu Asn Leu Gly Ser Leu Arg Leu Leu Gln Ala Val Pro Glu
1185                1190                1195                1200
```

```
Glu Ile Arg Glu Phe Arg Ile Thr Ile Arg Ala Thr Asp Gln Gly Thr
        1205                1210                1215
Asp Pro Gly Pro Leu Ser Thr Asp Met Thr Phe Arg Val Val Phe Val
    1220                1225                1230
Pro Thr Gln Gly Glu Pro Arg Phe Ala Ser Ser Glu His Ala Val Ala
1235                1240                1245
Phe Ile Glu Lys Ser Ala Gly Met Glu Glu Ser His Gln Leu Pro Leu
    1250                1255                1260
Ala Gln Asp Ile Lys Asn His Leu Cys Glu Asp Asp Cys His Ser Ile
1265                1270                1275                1280
Tyr Tyr Arg Ile Ile Asp Gly Asn Ser Glu Gly His Phe Gly Leu Asp
        1285                1290                1295
Pro Val Arg Asn Arg Leu Phe Leu Lys Lys Glu Leu Ile Arg Glu Gln
            1300                1305                1310
Ser Ala Ser His Thr Leu Gln Val Ala Ala Ser Asn Ser Pro Asp Gly
        1315                1320                1325
Gly Ile Pro Leu Pro Ala Ser Ile Leu Thr Val Thr Val Thr Val Arg
    1330                1335                1340
Glu Ala Asp Pro Arg Pro Val Phe Val Arg Glu Leu Tyr Thr Ala Gly
1345                1350                1355                1360
Ile Ser Thr Ala Asp Ser Ile Gly Arg Glu Leu Leu Arg Leu His Ala
        1365                1370                1375
Thr Gln Ser Glu Gly Ser Ala Ile Thr Tyr Ala Ile Asp Tyr Asp Thr
            1380                1385                1390
Met Val Val Asp Pro Ser Leu Glu Ala Val Arg Gln Ser Ala Phe Val
        1395                1400                1405
Leu Asn Ala Gln Thr Gly Val Leu Thr Leu Asn Ile Gln Pro Thr Ala
    1410                1415                1420
Thr Met His Gly Leu Phe Lys Phe Glu Val Thr Ala Thr Asp Thr Ala
1425                1430                1435                1440
Gly Ala Gln Asp Arg Thr Asp Val Thr Val Tyr Val Val Ser Ser Gln
        1445                1450                1455
Asn Arg Val Tyr Phe Val Phe Val Asn Thr Leu Gln Gln Val Glu Asp
            1460                1465                1470
Asn Arg Asp Phe Ile Ala Asp Thr Phe Ser Ala Gly Phe Asn Met Thr
        1475                1480                1485
Cys Asn Ile Asp Gln Val Val Pro Ala Asn Asp Pro Val Thr Gly Val
    1490                1495                1500
Ala Leu Glu His Ser Thr Gln Met Ala Ala Thr Ser Tyr Gly Thr Thr
1505                1510                1515                1520
Tyr Pro Tyr Ser Leu Met Arg
            1525

<210> SEQ ID NO 13
<211> LENGTH: 27
<212> TYPE: DNA
<213> ORGANISM: Heliothis virescens
<220> FEATURE:
<221> NAME/KEY: CDS
<222> LOCATION: (1)..(27)

<400> SEQUENCE: 13 tac aac acc aac act gcc caa ctg gtg                         27
Tyr Asn Thr Asn Thr Ala Gln Leu Val
  1               5
```

```
<210> SEQ ID NO 14
<211> LENGTH: 9
<212> TYPE: PRT
<213> ORGANISM: Heliothis virescens

<400> SEQUENCE: 14

Tyr Asn Thr Asn Thr Ala Gln Leu Val
  1               5

<210> SEQ ID NO 15
<211> LENGTH: 287
<212> TYPE: DNA
<213> ORGANISM: Heliothis virescens

<400> SEQUENCE: 15
tacaacacca acactgcctg ttccggactg tcacatcgcg ccggcctatg aggtcgcgcc    60
agcacacgtc atcgtgcgcc ccacctaagc tgggccctca ccatacgccg gaccccggga  120
cactcgctca gcgaccccgg tcgcgcatac acgaccgcac gggcaacgcg cgattttctc  180
ttgtacatac ttcaatacag tcttctttgc aaatcgaagt ttcattgaac cgccgagacc  240
atcatcctac atctggacct cggcgctcaa gcattggtcc ctcgcaa                287

<210> SEQ ID NO 16
<211> LENGTH: 291
<212> TYPE: DNA
<213> ORGANISM: Heliothis virescens

<400> SEQUENCE: 16
gcttcaaccc ggggaatatg ttcggactgt cacatcgcgc cggcctatga ggtcgcgcca     60
gcacacgtca tcgtgcgccc cacctaagct gggccctcac catacgccgg accccggac    120 actcgctcat cgaccccggt cgcgcataca cgaccgcacg cgcaacgcgc gatctactct   180
tgtcacctat ctataataca gtcttctact ttgaacatcg aagttttatt gaaacgccga   240
gaccagcaac ctacacctgc acctcggcgc tcaaacactg cccaactggt g            291
```

POLYNUCLEOTIDE ENCODING A GENE CONFERRING RESISTANCE TO *BACILLUS THURINGIENSIS* TOXINS

RELATED APPLICATIONS

This application claims the benefit of U.S. provisional application having Ser. No. 60/276,180 filed on Mar. 15, 2001, and which is incorporated herein by reference.

STATEMENT AS TO RIGHTS TO INVENTIONS MADE UNDER FEDERALLY SPONSORED RESEARCH AND DEVELOPMENT

The United States Government may have rights to this invention under the terms of a sponsored research agreement by the National Science Foundation, grant number MCB-9816056.

FIELD OF THE INVENTION

This invention is directed towards the occurrence and identification of pesticide tolerance of certain insects. The invention makes use of specific polynucleotide sequences associated with the onset of resistance to *Bacillus thuringiensis* toxins which are used as probes to monitor the presence of acquired insect resistance associated with transgenic crops. The specific polynucleotide sequences are also used to monitor changes in the frequencies of alleles which confer the resistance to the toxins.

BACKGROUND OF THE INVENTION

The bacterium *Bacillus thuringiensis* (Bt) contains genes encoding insecticidal proteins. Bt proteins are toxic when ingested by susceptible insect larvae. The protein attacks the insect's midgut, causes cessation of feeding, and eventually kills the insect. Bt toxins have been produced as fermentation products of Bt cultures and used in spray formulations for crop protection. Bt genes have also been used commercially to transform crop plants; these transgenic crop plants' cells then produce the insecticidal protein which attacks susceptible insects that attempt to feed on the plant.

The general mode of action of Bt toxins is well known in the art and is described for example by Rajamohan F, Lee M K, Dean D H (1998) *Progress in Nucleic Acid Research and Molecular Biology* 60: 1–27. The protein produced by the bacterium is usually a protoxin, which itself is not toxic until it is proteolytically cleaved by the insect's own proteases. The smaller protein resulting from proteolysis is the active toxin. This toxin diffuses through the peritrophic membrane to the midgut epithelium, where it binds to one or more sites in the membrane. This initial binding step may be reversible, but eventually the toxin becomes irreversibly bound to the membrane. A conformational change occurs in the toxin, whereby membrane-spanning alpha helices are inserted into the membrane, where they aggregate and form pores. These pores disrupt the normal osmotic balance of the epithelial cells. The cells swell and lyse, leading to destruction of the midgut epithelial cell layer and eventual death of the insect.

The initial binding step is believed to be necessary for toxin action; consequently there have been many studies on binding interactions of Bt toxins and components of the midgut, described for example by Pietrantonio P V and Gill S S (1996) in *Biology of the Insect Midgut*, Chapman & Hall, London, pp 345–372. Techniques used to study binding often start with the isolation of a brush border membrane vesicles (BBMVs) from the microvillar portion of columnar epithelial cells. Binding to BBMVs in suspension can be measured using labeled toxin. Alternatively, proteins can be isolated from BBMVs, separated by denaturing electrophoresis conditions, transferred to membranes, and probed with toxin. In addition, histological sections of insect midguts can be prepared and binding of labeled toxin can be visualized using microscopy.

Binding of Bt toxins to specific insect proteins can also be measured. Several proteins that interact with Bt toxins are well known in the art. Aminopeptidases exist in many different forms in insect midguts, and many of them have been shown to bind Bt toxins (Knight P J K, Knowles B H, Ellar D J (1995) *Journal of Biological Chemistry* 270 (30): 17765–17770; Gill S S, Cowles E A, Francis V (1995) *Journal of Biological Chemistry* 270 (45): 27277–27282; Luo K, Sangadala S, Masson L, Mazza A, Brousseau R, Adang M J (1997) *Insect Biochemistry and Molecular Biology* 27 (8-9): 735–743). Members of the cadherin superfamily have also been shown to bind Bt toxins (Vadlamudi R K, Weber E, Ji I H, Ji T H, and Bulla L A (1995) *Journal of Biological Chemistry* 270: 5490–5494; and Nagamatsu Y, Koike T, Sasaki K, Yoshimoto A, Furukawa Y, (1999) *FEBS Letters* 460: 385–390). Phosphatase enzymes have also been implicated in Bt toxin binding (Sangadala S, Walters F S, English L H, Adang M J, (1994) *Journal of Biological Chemistry* 269 (13): 10088–10092). TPP-75, an elastase-like serine protease, binds to certain Bt toxins and causes them to precipitate (Milne R E, Pang A S D, Kaplan H (1995) *Insect Biochemistry and Molecular Biology* 25 (10): 1101–1114). BTR-270, a peptidoglycan, binds Cry1A toxins with high affinity (Valaitis A P, Jenkins J L, Lee M K, Dean D H, Garner K J (2001) *Archives of Insect Biochemistry and Physiology* 46 (4): 186–200). Bt toxins have also been shown to bind to nonprotein components of midgut epithelial membranes. Glycolipids from *Manduca sexta* have been shown to bind Cry1A toxins using an overlay technique (Garczynski S F and Adang M J (2000) in *Entomopathogenic Bacteria: From Laboratory to Field Application*, Kluwer Academic Publishers, pp 181–197). Neutral lipids are involved in Bt toxin binding to *Manduca sexta* brush border membranes (Sangadala S, Azadi P, Carlson R, Adang M J (2001) *Insect Biochemistry and Molecular Biology* 32 (1): 97–107). Neutral glycolipids, especially hexa- and trisaccharylceramides, are implicated in Cry1A toxin binding in diamondback moth (Kumaraswami N S, Maruyama T, Kurabe S, Kishimoto T, Mitsui T, Hori H, (2001) *Comparative Biochemistry and Physiology B-Biochemistry & Molecular Biology* 129 (1): 173–183).

The relationship between binding targets for Bt-toxins and susceptibility or resistance to Bt is very complicated and not completely understood at the present time. Several hundred strains of *Bacillus thuringiensis* exist, with considerable specificity toward various groups of insects. Co-evolution between the insects and Bt has resulted in specificity of the interaction between Bt-toxin and the membranes of insect gut cells. The Bt-toxin of a particular strain of *Bacillus thuringiensis* may bind to the gut of some insect larvae but not to others. Thus, the Bt-toxins may have a high specificity for a small number of insect pest species while having no significant activity against beneficial insects, wildlife, or humans.

Plants transformed to carry Bt genes and express insecticidal proteins are known in the art and include potato, cotton, tomato, corn, tobacco, lettuce, and canola. Transformed plants are known in the art as reflected in U.S. Pat. Nos. 5,608,142; 5,495,071; 5,349,124; and 5,254,799, the specifications of which are incorporated in their entirety herein by reference. The use of genetically engineered plants is designed to reduce the use of broad spectrum insecticides.

There is concern that resistance may evolve to Bt toxins, whether they are applied to plants in spray formulations or the plants are genetically engineered to express them. The development of resistance to Bt-toxin expressing crops may also result in resistance to commercial formulations of fermented strains of Bt such as DIPEL® (Abbott Laboratories).

Rapid, reliable methods for broad screening to distinguish and detect the development of Bt resistance in populations of insects are needed. Heretofore, all methods require living or fresh-frozen insect larvae or preparations derived from them. The simplest methods employ bioassays on living insects, in which survivorship or larval metabolic rates are determined over time following a diet containing a specified concentration of a Bt-toxin. One such bioassay based on reduced metabolic rates after exposure to low doses of toxin mixed into artificial diet is discussed in U.S. Pat. No. 6,060,039 to Roe et al. which is incorporated herein by reference. Other bioassays are based on survival after exposure to a single, high diagnostic dose of toxin (for example, Diaz-Gomez O, Rodriguez J C, Shelton A M, Lagunes-T A, Bujanos-M R, (2000) *Journal of Economic Entomology* 93 (3): 963–970).

In principle, these bioassay methods can detect resistance no matter what its biochemical or physiological mechanism is. However, they require living, healthy larvae for their use, which are not always available. A more severe limitation on these methods is that, depending on the frequency of resistance genes in the populations, millions of individuals may need to be tested to detect a single resistant larva. High-level resistance to Bt is usually recessive, which means that an insect must have two copies of the resistance gene to be resistant. To a very good approximation, the frequency of such homozygous individuals is given by the square of the frequency of the resistance allele. For example, if the resistance allele frequency is one in a thousand, the frequency of homozygous resistant individuals is one in a million. In this example, more than a million larvae would need to be screened to detect resistance.

One solution to this problem is to develop methods for detecting the resistance genes directly. In the example just given, the frequency of heterozygous carriers of one copy of the resistance allele is 2×0.001×0.999 or approximately 2 in a thousand. When resistance is recessive, these individuals would not be identified by bioassay because the one resistance allele they carry is not enough to make them fully resistant. But a direct, DNA-based method for detecting the resistance allele would identify these individuals, and sample sizes on the order of a thousand, rather than a million, would suffice.

The main limitation to developing DNA-based methods for detecting resistance alleles is that, up to now, the identity of resistance-causing genes has been unknown. In spite of much work on Bt toxin mode of action, prior to the invention described herein there has not been a demonstration of which genes, when mutated, actually cause resistance. Accordingly, there is room for variation and improvement in the art of screening assays useful in detecting the presence of genes conferring Bt resistance in natural populations.

SUMMARY OF THE INVENTION

It is one aspect of one of the present inventions to provide a genetic probe to identify and monitor resistance for the Bt-toxin in target insect populations. One such insect pest is the tobacco budworm (*Heliothis virescens*) which is a major economic pest of cotton.

It is yet another aspect of one of the present inventions to develop a DNA probe and assay protocol which distinguishes between the conditions of homozygotes and heterozygotes with respect to resistance to Bt in populations of *Heliothis virescens* and other insects.

It is yet another aspect of one of the present inventions to provide a process and useful sequences in which nucleotide probes are used to monitor the presence of acquired insect resistance associated with a transgenic crop.

It is yet another aspect of one of the present inventions to provide a process and useful nucleotide sequences which are used to monitor population changes in the frequency of alleles which are associated with the resistance to Bt toxin.

These and other features, aspects, and advantages of the present invention will become better understood with reference to the following description and appended claims.

BRIEF DESCRIPTION OF THE DRAWINGS

A full and enabling disclosure of the present invention, including the best mode thereof, to one of ordinary skill in the art, is set forth more particularly in the remainder of the specification, including reference to the accompanying drawings.

BRIEF DESCRIPTION OF THE SEQUENCE LISTINGS

Figure 1:
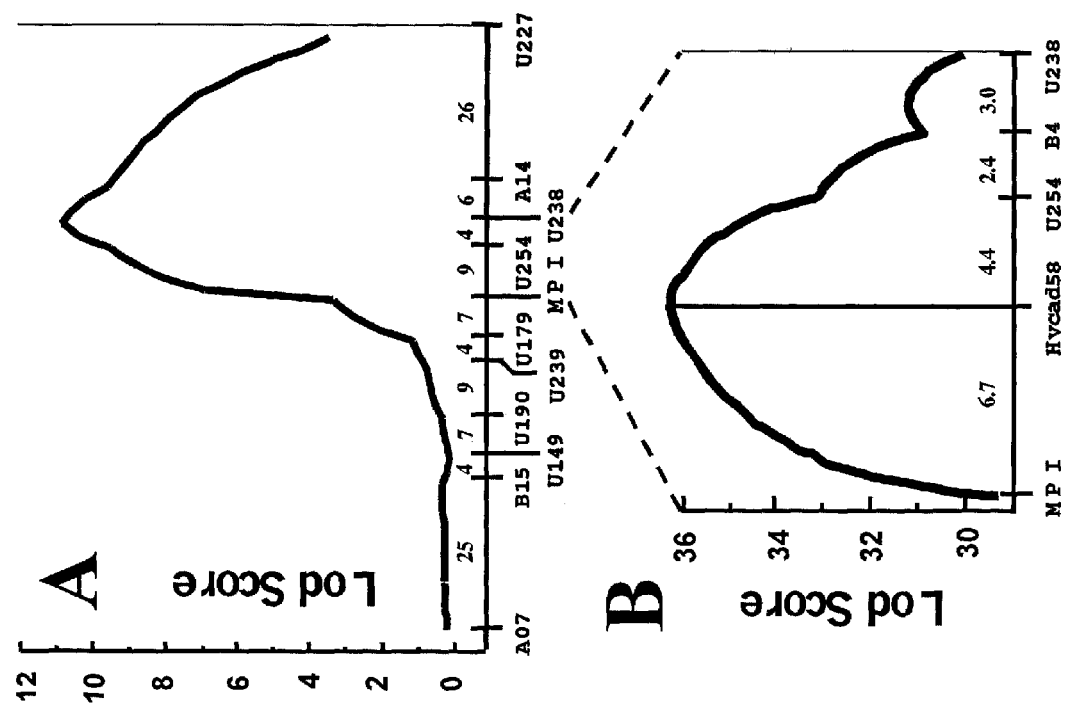
FIG. 1 is a QTL map of the Cry1Ac resistance trait on linkage group 9 of *Heliothis virescens*.

The accompanying sequence ID listings are identified below. The sequence listings appear following the claims and are incorporated herein by reference.

The first sequence 1 identifies SEQ ID NO: 1 which is the DNA sequence of the susceptible allele s1 of HevCaLP.

Sequence 2 is the protein sequence SEQ ID NO: 2 of a conceptual translation of allele s1 as used in the protein alignment to *Bombyx* and *Manduca*.

Sequence 3 is the DNA sequence of SEQ ID NO: 3 which is the resistant allele r1 of HevCaLP, including the Hel-1 insert and the duplicated target sequences.

Sequence 4 is the DNA insert identified as SEQ ID NO: 4 for the Hel-1 insert which does not include duplicated target sequences.

Sequence 5, having SEQ ID NO: 5, is a DNA sequence corresponding to the left LTR of the Hel-1 insert.

Sequence 6, having SEQ ID NO: 6, is a DNA sequence corresponding to the right LTR of the Hel-1 insert.

Sequence 7, having SEQ ID NO: 7, is a DNA sequence of primer F1 corresponding to bases 1982 to 2001 of SEQ ID NO: 3.

Sequence 8, having SEQ ID NO: 8, is a DNA sequence corresponding to primer R2 consisting of the reverse complement of bases 4322 to 4351 of SEQ ID NO: 3.

Sequence 9, having SEQ ID NO: 9, is a DNA sequence corresponding to primer R3 consisting of the reverse complement of bases 2029 to 2052 of SEQ ID NO: 3.

DESCRIPTION OF THE PREFERRED EMBODIMENT

Reference now will be made in detail to the embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention cover such modifications and variations as come within the scope of the appended claims and their equivalents. Other objects, features, and aspects of the present invention are disclosed in the following detailed description. It is to be understood by one of ordinary skill in the art that the present discussion is a description of exemplary embodiments only and is not intended as limiting the broader aspects of the present invention, which broader aspects are embodied in the exemplary constructions.

In describing the various figures herein, the same reference numbers are used throughout to describe the same material, apparatus or process pathway. To avoid redundancy, detailed descriptions of much of the apparatus once described in relation to a figure is not repeated in the descriptions of subsequent figures, although such apparatus or process is labeled with the same reference numbers.

Applicants' protocols and procedures may be found in reference to "*Identification of a Gene Associated with Bt resistance in Heliothis virescens*" which was published in Science, volume 293, pp 857–860, on Aug. 3, 2001; and which is incorporated herein by reference.

A resistant strain of *Heliothis virescens* was previously developed in the laboratory by selection using artificial diet containing various concentrations of Bt toxin (Gould F, Anderson A, Reynolds A, Bumgarner L, Moar W (1995) *Journal of Economic Entomology* 88 (6): 1545–1559). The strain, named YHD2, is 10,000 fold more resistant to the toxin Cry1Ac and is conditioned in a large part by a single recessive gene named BtR-4 which is located in linkage group 9 of *H. virescens*. The initial localization of the resistance gene BtR4 has been reported in the Applicants' prior publication (Heckel D G, Gahan L C, Gould F, Anderson A (1997) *Journal of Economic Entomology* 90: 75–86) and which is incorporated herein by reference.

Further localization of BtR-4 to a particular region of linkage group 9 was carried out using a total of 11 polymorphic markers spanning a length of 105 cM. The markers were scored on a segregating backcross family derived from YHD2 females crossed with susceptible males. The linkage group was scanned for quantitative trait loci (QTLs) conferring Bt resistance following the methods of Lander, E S and Botstein D (1989) *Genetics* 121: 185–193. A single, highly significant peak of the log-likelihood function indicated that the BtR-4 resistance gene is located between A14 and MPI as set forth in FIG. 1.

The cadherin superfamily was chosen as a candidate for BtR-4. Partially degenerate oligonucleotide primers Bmtp5 and Bmtp8 as shown in Table 1 were designed based on published sequence of the BtR175 gene from *Bombyx mori* (GenBank Accession No AB026260, described by Nagamatsu Y, Toda S, Koike T, Miyoshi Y, Shigematsu S, Kogure M (1998) *Bioscience, Biotechnology and Biochemistry* 62 (4): 727–734). These primers were used in the polymerase chain reaction (PCR) with cDNA prepared from midgut mRNA of larval *Heliothis virescens*. A PCR product of 334 basepairs designated Hvcad58 was amplified, cloned and sequenced using conventional methodology well-known to those skilled in the art. The sequence of Hvcad58 corresponds to bases 4279 to 4612 of SEQ ID NO: 1.

Radiolabeled Hvcad58 was used to probe Southern filters made from additional segregating backcross families for further mapping on linkage group 9. Finer scale QTL mapping in this region using 268 backcross progeny yielded a single peak of the log-likelihood function directly above the map location of Hvcad58 (FIG. 1). The data clearly indicates that the gene containing Hvcad58 is a strong candidate for the BtR-4 resistance gene.

The Hvcad58 probe was used to screen midgut cDNA libraries made from resistant (YHD2) and susceptible strains of *Heliothis virescens*. Clones recovered from these libraries were sequenced and used to design additional primers to amplify the full-length coding sequence from susceptible cDNA. In addition to the cDNA methods, a five-prime RACE (rapid amplification of cDNA ends) technique was used to complete the full sequence.

Figure 2:
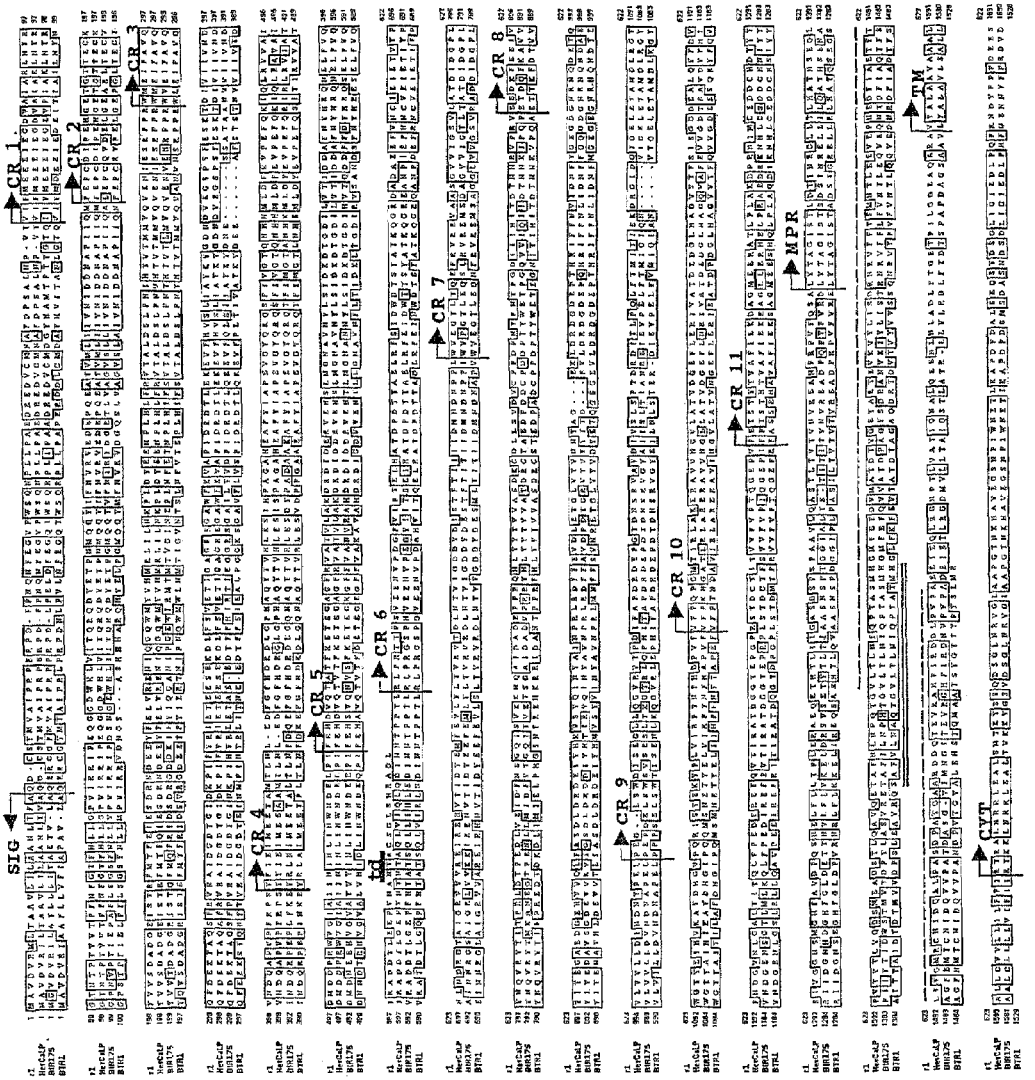
FIG. 2 is a conceptual translation of HevCaLP (s1 allele and r1 allele) in alignment with BmBtR175 of *Bombyx mori* and BtR1 of *Manduca sexta*.

The sequencing yielded one transcript (s1) cloned from a susceptible strain as given in SEQ ID NO: 1. Conceptual translation of this transcript produced a protein product (that we have named HevCaLP, *Heliothis virescens* cadherin-like protein) of 1732 amino acids as given in SEQ ID NO: 2. HevCaLP is 70% identical to the BtR175 protein, sharing a signal sequence at the amino terminus, 11 extra-cellular cadherin-type repeats, a non-cadherin proximal membrane region, a transmembrane region, and a highly conserved cytoplasmic domain at the carboxy terminus as shown in FIG. 2. It shows somewhat less similarity to the BT-R1 protein from *Manduca sexta*, as given in GenBank Accession No. AAB33758 and reported by Vadlamudi R K, Weber E, Ji I H, Ji T H, and Bulla L A (1995) *Journal of Biological Chemistry* 270: 5490–5494. The transmembrane and cytoplasmic domains are absent from that sequence of BT-R1.

Figure 3:
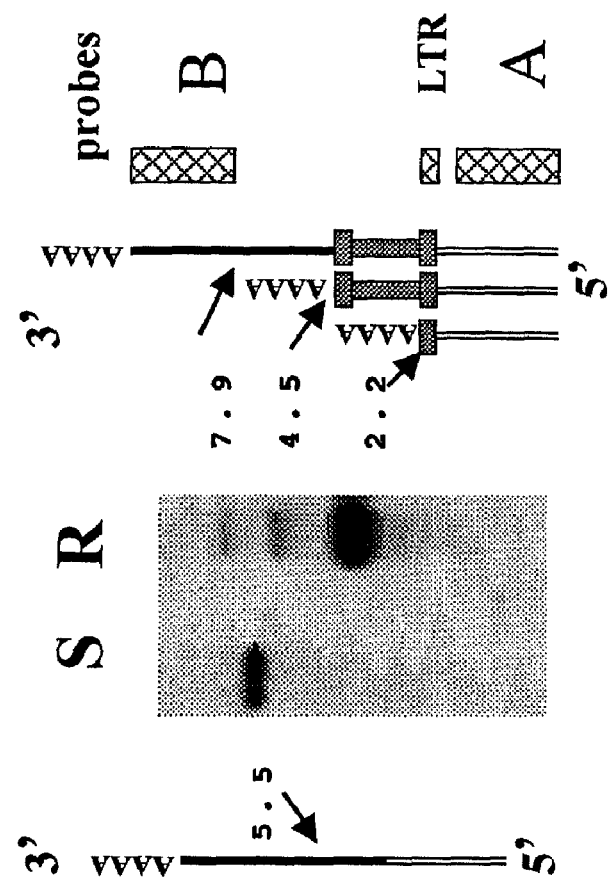
FIG. 3 is a northern analysis of mRNA isolated from susceptible and resistant strains following probing with the gene sequences set forth herein.
Figure 4:
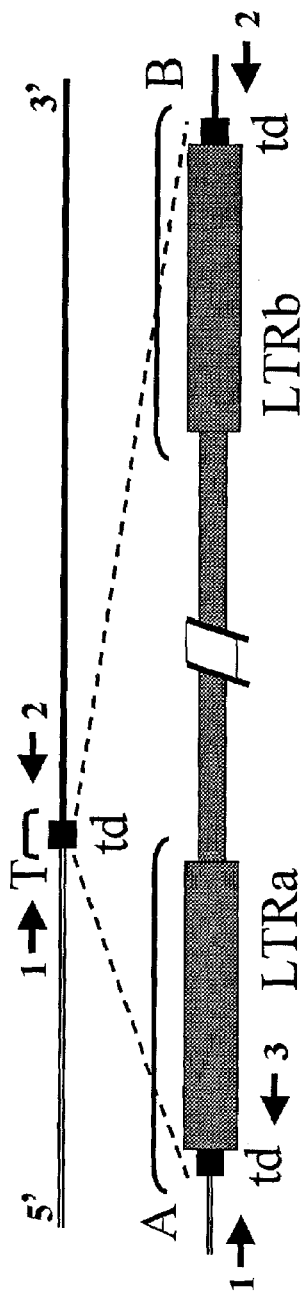
FIG. 4 sets forth the insertion point of the Hel-1 element in the r1 allele of HevCaLP.

Expression of the mRNA encoding HevCaLP in susceptible and resistant larval midguts was studied using northern analysis and sequencing of clones from the resistant library. As shown in FIG. 3, susceptible larvae show a single transcript of 5.5 kb. YHD2 larvae show three transcripts. The sequence of the rarest (7.9 kb) is denoted as the r1 allele, and given as set forth in SEQ ID NO: 3. It is similar to the susceptible transcript except for a 2.3 kb insert denoted as Hel-1 as given in the accompanying SEQ ID NO: 4. Hel-1 shows several hallmarks of the LTR-type retrotransposons. Hel-1 has an approximately 255 nucleotide long terminal repeat (LTR) sequence at both ends and an unrelated sequence in the middle. The left LTR sequence, LTRa, is given in SEQ ID NO: 5 and the right LTR sequence, LTRb, is given in SEQ ID NO: 6. Hel-1 is flanked by an 8-nt duplication of the host sequence ACACTGCC, as shown in FIG. 4. The transcript of intermediate abundance (4.4 kb) is an abbreviated form, truncated at the second LTR of Hel-1 by a poly-A tail. The third, highly abundant transcript (2.1 kb), is truncated at the first LTR of Hel-1 by a poly-A tail.

Because of an in-frame stop codon 30 bases into the first LTR of Hel-1, conceptual translation of the three different YHD2 transcripts produces the same truncated 622-aa protein (as shown in the translation of the r1 allele in FIG. 2). Multiple stop codons in all three reading frames of the LTR follow the initial stop codon, preventing translation of a larger protein containing the carboxy-terminus of HevCaLP. Thus, the predicted protein product of the YHD2 r1 allele (if one is produced) would possess the same signal sequence as HevCaLP (possibly directing its secretion into the midgut lumen) but no predicted transmembrane domain or toxin-binding region.

Figure 5:
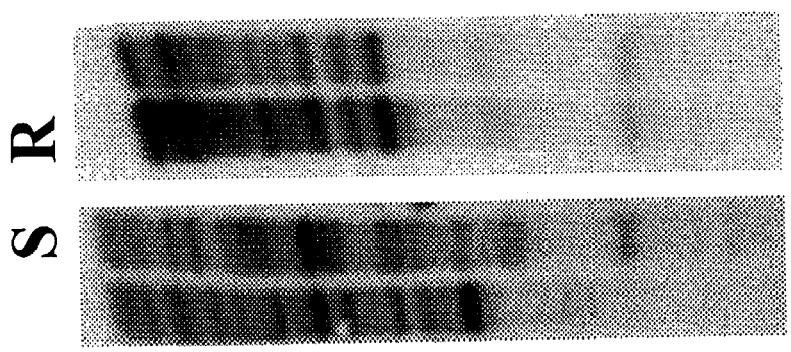
FIG. 5 shows the multi-copy occurrence of Hel-1 in genomic DNA of resistant and susceptible strains of *Heliothis virescens*.

Genomic Southern blots probed with the LTR region of Hel-1 show that it occurs with a copy number of 10-15 in both YHD2 and susceptible insects (FIG. 5). Insertion of this Hel-1 element into the gene encoding HevCaLP has created the novel, knockout r1 allele which confers resistance when homozygous (present in two copies in an individual insect). This insertion event could have occurred in the laboratory during the Bt-resistance selection protocol that produced YHD2, or may already have been present in the field-collected founders of the selection line. Thus it is now evident that a DNA-based method for detecting Bt resistance in *Heliothis virescens* may be devised, based on detection of the specific insertion of the Hel-1 element into the gene encoding HevCaLP, producing the r1 allele.

To illustrate detection of the r1 allele, a PCR assay was designed using two primers flanking the insertion point (F1 and R2) and a third (R3) internal to the left LTR (FIG. 4). Primer F1 consists of bases 1982 to 2001 of SEQ ID NO: 3, 5' ATA CGA GCT GAC GAC ACG CTG GGA GA 3', primer R2 consists of the reverse complement of bases 4322 to 4351 of SEQ ID NO: 3, 5' TCT GAG CGT AGG AGG TGT GTT GTT GAT GTC 3', and primer R3 consists of the reverse complement of bases 2029 to 2052 of SEQ ID NO: 3, 5' GCG CGA TGT GAC AGT CCG GM CAG 3'. Primers F1 and R3 produce a 71-bp band from the r1 allele. Primers F1 and R2 amplify a 99-bp band from s1 or other susceptible alleles lacking the Hel-1 insert. Heterozygotes produce both bands. This is a marked improvement on a conventional bioassay, which would not distinguish heterozygotes from homozygous susceptibles because the resistant allele is recessive. It also confirms that the resistant strain is fixed for the r1 allele, as all YHD2 individuals examined to date have the 71-bp band only. It will be evident to those skilled in the art that the detection method for the r1 alelle is not limited to PCR with these specific primers, and that there are many other molecular methods of detecting the specific insertion of the Hel-1 element into the HevCaLP gene, based on the sequence information disclosed herein.

It is believed that the gene encoding HevCaLP is identical to BtR-4, the major resistance gene in YHD2. Recessivity of the resistant allele at BtR-4 is explained by Hel-1 inactivation of HevCaLP. HevCaLP functions as a "lethal target" of Bt-toxin, since two copies of the disrupted allele are required for 10,000-fold resistance. Heterozygotes still present a "lethal target" since they have one copy of the susceptible allele.

The normal physiological function of HevCaLP is unknown, although other members of the cadherin superfamily are involved in cell adhesion and signalling (T. Uemura (1998) *Cell* 93 (7): 1095–1098). Whatever its function, it is not essential for life, as YHD2 is viable and fertile under laboratory conditions, despite being a "natural knockout" strain for HevCaLP. Whether its absence confers a fitness disadvantage in the field has important implications for resistance management, and this question can now be addressed with the information developed here. Target-site resistance to other insecticides usually involves modification but not knockout of the target, which is generally essential for life (e.g., acetylcholinesterase for organophosphates, sodium channel for pyrethroids, GABA receptor for cyclodienes) (French-Constant R H, Pittendrigh B, Vaughan A, Anthony N (1998) *Philosophical Transactions of the Royal Society of London Series B-Biological Sciences* 353 (1376): 1685–1693,). However, methoprene resistance in *Drosophila melanogaster* provides another example of resistance by gene inactivation (Wilson T G & Ashok M, (1998) *Proceedings of the National Academy of Sciences of the USA* 95 (24): 14040–14044).

The present invention now makes possible the application of molecular methods to Bt-resistance monitoring. We previously estimated the frequency of YHD2-type resistant alleles in field populations of *Heliothis virescens* prior to widespread planting of transgenic Bt-cotton to be 0.002 (Gould F, Anderson A, Jones A, Sumerford D, Heckel D G, Lopez J, Micinski S, Leonard R, Laster M (1997) *Proceedings of the National Academy of Sciences of the USA* 94 (8): 3519–3523). This labor-intensive, bioassay-based estimate was derived by testing progeny of more than 1,000 field-caught males mated to YHD2 females, for alleles which would confer resistance when heterozygous with r1. Our results now suggest that this estimate covers the entire class of HevCaLP knockouts regardless of the nature of the molecular lesion, as well as other mutants preventing any expressed HevCaLP from functioning as a toxic target. Development of efficient DNA-based methods to detect these other types of mutants at BtR4 should be a high priority and is now possible with the methods described herein.

Only by monitoring allele frequencies at resistance genes like BtR-4 will it be possible to verify that the high-dose/refuge resistance management strategy for Bt-cotton mandated by the US Environmental Protection Agency (EPA) is actually working to keep resistance allele levels low. The present invention affords a new method of complying with EPA regulations which require monitoring resistance levels in *Heliothis virescens*. The present invention provides a nucleic acid probe that will specifically identify genes for resistance in field populations. Further, the probes and protocols set forth herein provide for a method of monitoring the population of homozygous and heterozygous resistant individuals in field populations.

Bt resistance in *Heliothis virescens* caused by other types of mutations that inactivate the HevCaLP gene product may also be screened for using the information provided herein. Such methods may include obtaining portions of the gene or its homologues by cDNA cloning or the polymerase chain reaction, determining the DNA sequence by standard methods, and examining the sequence for the occurrence mutations that may include nucleotide substitution, insertions, or deletions. Such mutations may affect protein sequences encoded by the gene by causing amino acid substitutions, insertions, or deletions as well as incorrect intron splicing, premature chain termination due to nonsense mutations, or errors in the normal initiation or termination of the transcription or translation.

By way of example, DNA or RNA isolated from individual *Heliothis virescens* is used as the template for PCR using primers specifically designed from SEQ ID NO: 1. The PCR products are directly sequenced, or cloned and sequenced, using standard methods. The sequences are examined using commercially available computer programs well known in the art, such as the Wisconsin Genetics Computer Group package. Mutations, such as individual nucleotide substitutions, insertions, or deletions; or insertions or deletions of several nucleotides, are detected by comparison to SEQ ID NO: 1. Such mutations may alter the amino acid in the protein sequence, leading to reduced binding of Bt toxins to the HevCaLP gene product and thereby conferring resistance. Or such mutations may cause frameshifts or premature occurrence of stop codons, resulting in a truncated or absent protein that fails to bind to Bt toxins and thereby confers resistance.

In the course of this invention, an isolated nucleic acid molecule of the present invention includes a nucleic acid that is at least about 85%, preferably at least about 90%, and still more preferably at least about 95%, and even more preferably at least about 99% identical to the sequence of the susceptible allele s1 of HevCaLP. Additionally, any isolated polynucleotide or naturally occurring polynucleotide that hybridizes to the sequence set forth in SEQ ID NO: 1 at 60° C. in 1×SSC will have properties useful in carrying out the present invention.

Other embodiments of the present invention include isolated nucleic acid molecules that are at least about 85%, preferably at least about 90%, still more preferably at least about 95%, and even more preferably at least about 99%, identical to the sequences set forth in SEQ ID NO: 3 and SEQ ID NO: 4.

Bt resistance in other insect species may also be screened for using the same approach. These species may contain one or more genes homologous to the *Heliothis virescens* HevCaLP gene, whose products interact with Bt toxins. Resistance in these other species can be detected by obtaining the sequence of those genes, designing PCR primers, and amplifying and sequencing DNA from individual insects collected from the field or reared in the laboratory. Examination of the sequence for inactivating mutations as described herein will detect Bt resistance in those species. Representative sequences of HevCaLP homologues in other species and which may be used in the screening process described herein include the following:

1) *Manduca sexta* BT-R1, GenBank Accession No.I77078, U.S. Pat. No. 5,693,491 (SEQ ID NO: 1) and U.S. Pat. No. 6,007,981 (SEQ ID NO: 1);
2) *Bombyx mori* BtR175, GenBank Accession No. AB026260, described by Nagamatsu Y, Toda S, Koike T, Miyoshi Y, Shigematsu S, Kogure M (1998) Bioscience, Biotechnology and Biochemistry 62 (4): 727–734;
3) *Pectinophora gossypiella* BT-R2, GenBank Accession No. AX150183, Patent Application, International Publication No. WO01/34807 (SEQ ID NO: 1);
4) *Ostrinia nubilalis*, GenBank Accession No. AX147201, Patent application, International Publication No. WO 01/36639 (SEQ ID NO: 1);
5) *Helicoverpa zea*, GenBank Accession No. AX147203, Patent application, International Publication No. WO01/36639 (SEQ ID NO: 3);
6) *Spodoptera frugiperda*, GenBank Accession No. AX147205, Patent application, International Publication No. WO0/136639 (SEQ ID NO: 5); and
7) *Lymantria dispar* BTR-CAD, GenBank Accession No. AF317621.

The above identified sequences and the referenced publications are all incorporated herein by reference as is set forth in their entirety.

The current methodology includes detecting resistance to *Bacillus thuringiensis* endotoxin in insect populations by screening for mutations that alter the structure or function of a protein as set forth in SEQ ID NO: 2. For the purposes of screening protocols, it is believed that using the sequence set forth in SEQ ID NO: 2 may include homologues and other species which would display at least 60% similarity to the sequence set forth in SEQ ID NO: 2. More preferably, the sequence similarity is at least about 75%, preferably at least about 80%, more preferably at least about 85%, even more preferably at least about 90%, still more preferably at least about 95%, and even more preferably at least about 99% identical to the amino acid sequence set forth in SEQ. ID. NO: 2.

Several of the mutations in other species detected by this approach may not have an obvious effect of activating the HevCaLP homologue. In that case, evidence that the mutation confers resistance may be obtained by conducting a linkage analysis and mapping the gene as described herein for *Heliothis virescens*. For that purpose, a strain of the species of interest with the mutation is crossed with a wild-type strain, and the F1 hybrids are intercrossed or backcrossed to one of the parental strains. The F2 or backcross progeny are tested for resistance by any of the bioassay methods described previously and well known in the art, and DNA is isolated from each individual progeny. The DNA is analyzed for the presence of the mutation, using restriction fragment polymorphism analysis, allele-specific PCR, denaturing gradient gel electrophoresis, single-stranded conformation polymorphism, denaturing high-performance liquid chromatography, or any other mutation detection system well known in the art. Evidence that the mutation confers resistance is obtained from the correlation across progeny between presence of the mutation and presence of resistance.

A straightforward extension of this method of detecting Bt- resistance is to examine the DNA sequence of genes encoding other proteins that interact with Bt toxins, including but not limited to aminopeptidases, alkaline phosphatases, elastin-like serine proteases, and peptidoglycans.

All cited references, publications, and sequence listings set forth herein are incorporated by reference in their entirety.

These and other modifications and variations to the present invention may be practiced by those of ordinary skill in the art, without departing from the spirit and scope of the present invention. In addition, it should be understood that aspects of the various embodiments may be interchanged both in whole or in part. Furthermore, those of ordinary skill in the art will appreciate that the foregoing description is by way of example only, and is not intended to limit the invention.

TABLE 1

Primers Used in Determining the Structure of BtR4, the Cadherin-like Polynucleotide in *Heliothis virescens*

| | |
|---|---|
| Bmtp 5 | 5'-GTR CTG ACK GTT AAY ATC GAG CCC ACK GC-3' |
| Smtp 8 | 5'-TAG GGG YAC RTT RTC SCG KAT GAA GTG KCC-3' |
| Hvtp05 | 5'-AGC CCA CTG CAT CTA TGC ACG GCA TGT TTG A-3' |
| Hvtp08 | 5'-CCT GAG TTG GGT CTG GTG GTC CCT GGC-3' |

TABLE 1-continued

Primers Used in Determining the Structure of BtR4, the Cadherin-like Polynucleotide in *Heliothis virescens*

| | |
|---|---|
| GGp1 | 5'-TGT GGA GTC AGC TTC CAT AGA GTC TTG TAT GAG CGT GTA-3' |
| CGnotp2 | 5'-GAT ACG CGG CCG CAG GTC AGC AGA GCT CTG TTG ATG GTG TCG AGG GTG GAG A-3' |
| T7p1 | 5'-TAA GTT GGG TAA CGC GAG GGT TTT CCC AGT GAC-3' |
| T7p2 | 5'-GGC CAG TGA ATT GTA ATA CGA CTC ACT ATA GGG CG-3' |
| T3p1 | 5'-GAT AAC AAT TTC ACA CAG GAA ACA GCT ATG ACC ATG-3' |
| T3p2 | 5'-GAA ATT AAC CAC CCT TAA AGG GAA CAA AAG CTG GAG-3' |
| CGp3 | 5'-GGC ACG TTT TTT TCC ACT GAC GGG GTC GTG CG-3' |
| Cgnotp4 | 5'-GAT ACG CGG CCG CGG GCA GTC TGA GCG TAG GAG GTG TGT TGT TGA T-3' |
| RC36T4 | 5'-GAC GTG TGT TCG CCT GAT CCT AAC TAC T-3' |
| RC36cg5 | 5'-AGC CTC TTA AAT CCA TAG GGG TCT CCA G-3' |
| RC36cg5+ | 5'-CTG GAG ACC GCT ATG GAT TTA AGA-3' |
| SC3T6 | 5'-ATG TTC GAG GTG CTG TAC CTC ACC G-3' |
| SC3cg7 | 5'-ACA CGA ACA CAG GAT CGT GGA AGT T-3' |
| CGp5 | 5'-TGT ATC TTC TGG AAC TCC GGC ACT TCG AAG TC-3' |
| CGnotp6 | 5'-GAT ACG CGG CCG CAT GTG ATG GTT CTG CGT GCC GAC GAT GAA GGA CTG-3' |
| Sint1 | 5'-GCT AAG GAC CGG GAT ATT GAT GAT AGA GT-3' |
| Sint2 | 5'-CGT GCG GGG CAG TCT GAG AGT AG-3' |
| RUNI1 | 5'-CAT ACA CGA CCG CAC GCG CAA CG-3' |
| RUNI2 | 5'-TGA GCG CCG AGG TGC AGG TGT AGG-3' |
| Hvtp13 | 5'-CTG TAC ACA GCC GGC ATC TCC AC-3' |
| Hvtp14 | 5'-CTG GAA GTT GAG GGT CAG CAC TCC AGT-3' |
| Hvtp15 | 5'-AAC CGT CGT CTG GAA GCT CT-3' |
| Hvtp16 | 5'-TCT TCG ATG CCG ATC AGA TCC GAG TC-3' |
| Hvtp17 | 5'-GCG GCG CCG GGC ACC AAC AAG CA-3' |
| HvA11-RT | 5'-AAT AGA TGC TCT TAC ATA ATA CGA GTA TCT TAC-3' |
| 5'R5A4/8 | 5'-GAT ACG CGG CCG CGA GAA CTA TGA GAT GGC AGT CGA CGT GAG AAT A-3' |
| HvA11F1 | 5'-GAA CTA TGA GAT GGC AGT CGA CGT GAG AAT-3' |
| HvA11F3 | 5'-TTA ACT TTC GCG CAA GAT TGT TCC TAT ATG-3' |
| HvA11R2 | 5'-GAA CTC TGG GCT GAA GGG GGT AGC-3' |
| HvA11R4 | 5'-CCC GAA GTT RTT GTT ATG GTT TGC TAC TGA-3' |
| USTP01 | 5'-ATG GGC AAC GCA GTT AAC TAC CTG-3' |
| USTP02 | 5'-CAT CCT CGT GAC AAT CGA CGA TGC-3' |
| USTP03 | 5'-CAG ACA GAA CGA GCT CTT TGT GCA-3' |
| F771-5Ksp1 | 5'-GCC GTG CAG CAG TTC GAT GAG AAG-3' |
| F771-5Ksp2 | 5'-CTC CCA CTG TAT CAG TAG CCA TCA-3' |
| 738-3.4Ksp1 | 5'-ACA ATC CTT CAG GGT TCG AGC CAT C-3' |
| 738-3.4Ksp2 | 5'-GTA CAA GAG AAA ATC GCG CGT TGC GT-3' |
| 738-3.4Ksp3 | 5'-CCT GAT CAA CTG GAA CGA TGA GCT G-3' |
| 738-3.4Ksp4 | 5'-CCA AAG TCC ACG GGC GGT TGC GCA C-3' |
| 738-3.8sp6 | 5'-GTG TAA CGT AGT GTG CTC GTG TAA TGC-3' |
| 738-C10sp8- | 5'-CCG TCT GAA ACA TGT CGA AGT CAT-3' |
| TBR01 | 5'-GAG ACT AGC ACC TAC ACG GTC GCT-3' |
| TBR02 | 5'-TCC AAC GAG CTG TTC CTG CTG ACG-3' |
| CR9TBR | 5'-CAC TGT TAC TGT CAA TGT TCG AGA-3' |
| LTR-Pr1 | 5'-CAC ACG TCA TCG TGC GCC CCA CCT AAG CTG-3' |
| LTR-Pr2 | 5'-CTG GCG CGA CCT CAT AGG CCG GCG CGA TGT-3' |
| LTR-1.9Ksp1 | 5'-CGA ATC AGC TGA TTC ATT GTC GCT-3' |
| LTR-1.9Ksp2 | 5'-GTA GTG TGT GAT GTG ATC CAG-3' |
| Rint-Fwd1 | 5'-ATA CGA GCT GAC GAC ACG CTG GGA GAG CC-3' |
| Rint-Rev2 | 5'-TCT GAG CGT AGG AGG TGT GTT GTT GAT GTC-3' |
| C36RESEQ-F | 5'-CCC GGC ACC GAC AAC TCC-3' |
| C36RESEQ-R | 5'-CTC CAT GGT CGT ATG CCT TGA CAT GTA-3' |
| pc11Fa | 5'-GAG ATG GCA GTC GAC GTG AGA ATA CTG A-3' |
| pc12Fa | 5'-CCC GTT TCG CCG TGT TCA GGA ATG TC-3' |
| pc12Ra | 5'-TGG TAC CTC GGT AGT TAA GCC TGG CAA T-3' |
| pc13Fa | 5'-GAA CAC GGC GAA ACG GGC ACC ACA GA-3' |
| pc13Ra | 5'-TGC CAG GCT TAA CTA CCG AGG TAC CA-3' |
| pc14Fa | 5'-AAC CCG CTG CAT TTG TTT AGA GTT ACA G-3' |
| pc14Ra | 5'-CGA ACT GCT GCA CGG CGA AGA TCT CCA T-3' |
| pc15Ra | 5'-TTC CTT CCA CGT CAT TGT CGC CAT ATT T-3' |
| RintS-F1 | 5'-ATA CGA GCT GAC GAC ACG CTG GGA GA-3' |
| RintS-R2 | 5'-TCT GAG CGT AGG AGG TGT GTT GTT GAT GTC-3' |
| RintR-R3 | 5'-GCG CGA TGT GAC AGT CCG GAA CAG-3' |
| RintR-F4 | 5'-ACG CGC AAC GCG CGA TCT ACT CTT-3' |

That which is claimed is:

1. A method of detecting resistance to *Bacillus thuringiensis* endotoxin in *Heliothis virescens* populations by screening for the presence of mutations having a sequence selected from the group consisting of SEQ ID NO: 3 or SEQ ID NO: 4.

2. A method of detecting resistance to *Bacillus thuringiensis* endotoxin in insect populations by screening for mutations that alter the structure or function of any protein encoded by the nucleotide sequence set forth in SEQ ID NO: 1.

3. A method of detecting resistance to *Bacillus thuringiensis* endotoxin in insect populations by screening for mutations that alter the structure or function of SEQ ID NO: 2 or homologues of SEQ ID NO: 2, wherein SEQ ID NO:2 and said homologues of SEQ ID NO: 2 bind *Bacillus thuringiensis* endotoxin.

4. A method for detecting mutations in genes from insect populations by screening for the presence of insertions of a DNA sequence that hybridizes to SEQ ID NO: 4 or the complement of SEQ ID NO: 4 at 60° C. in 1×SSC.

5. A process for monitoring Bt resistance associated with the presence of an r1 allele in an insect population associated with transgenic crops comprising the steps of:
   obtaining DNA from an individual insect;
   amplifying said DNA using primers having nucleotide sequences of SEQ ID NO: 7, SEQ ID NO: 8, and SEQ ID NO: 9.
   measuring the molecular size of said amplified DNA, thereby determining whether said individual has zero, one, or two copies of said r1 allele.

6. A method of detecting mutations in purified nucleic acid sequences obtained from an insect population by screening for a sequence of at least 24 contiguous nucleotides, wherein the at least 24 contiguous nucleotides are on a sequence selected from the group consisting of SEQ ID NO: 4, SEQ ID NO: 5, and SEQ ID NO: 6.

7. A method of detecting resistance to *Bacillus thuringiensis* endotoxin in insect populations by:
   providing purified genomic DNA from an individual insect;
   performing PCR using oligonucleotide primers of 24 nucleotides or greater, identical in at least 16 positions of 24 to any sequence of 24 contiguous nucleotides of SEQ ID NO: 1 or the complement of SEQ ID NO: 1;

determining the DNA sequences of the PCR products;

computing the conceptual translations of the DNA sequences of the PCR products in all six reading frames;

comparing each of the predicted polypeptide sequences to SEQ ID NO: 2 or homologues thereof, wherein SEQ ID NO:2 and said homologues of SEQ ID NO: 2 bind *Bacillus thuringiensis* endotoxin;

whereupon the comparison, if indicating any change that would lead to the premature termination of the protein such that the last 12 amino acids or more of the carboxy-terminus of SEQ ID NO: 2 or homologues thereof would be predicted to be lacking in the mature protein, the insect will be at least heterozygous for resistance to *Bacillus thuringiensis* endotoxin.

* * * * *